(12) United States Patent
Park et al.

(10) Patent No.: US 9,400,281 B2
(45) Date of Patent: Jul. 26, 2016

(54) METHOD OF SCREENING OF THERAPEUTIC AGENTS FOR K-RAS MUTANT DRIVEN CANCERS

(71) Applicants: PUSAN NATIONAL UNIVERSITY INDUSTRY-UNIVERSITY COOPERATION FOUNDATION, Pusan (KR); THE INDUSTRY & ACADEMIC COOPERATION IN CHUNGNAM NATIONAL UNIVERSITY, Daejeon (KR)

(72) Inventors: Bum Joon Park, Busan (KR); Nam Chul Ha, Busan (KR); Sun Hye Lee, Busan (KR); Gyu Yong Song, Daejeon (KR); Jee Hyun Lee, Daejeon (KR)

(73) Assignees: PUSAN NATIONAL UNIVERSITY INDUSTRY-UNIVERSITY COOPERATION FOUNDATION, Pusan (KR); THE INDUSTRY & ACADEMIC COOPERATION IN CHUNGNAM NATIONAL UNIVERSITY, Daejeon (KR)

( * ) Notice: Subject to any disclaimer, the term of this patent is extended or adjusted under 35 U.S.C. 154(b) by 0 days.

(21) Appl. No.: 14/144,603

(22) Filed: Dec. 31, 2013

(65) Prior Publication Data

US 2014/0147866 A1 May 29, 2014

Related U.S. Application Data

(62) Division of application No. 13/130,159, filed as application No. PCT/KR2009/006896 on Nov. 23, 2009, now abandoned.

(30) Foreign Application Priority Data

| Nov. 21, 2008 | (KR) | 10-2008-0116343 |
| Mar. 5, 2009 | (KR) | 10-2009-0018956 |
| Aug. 17, 2009 | (KR) | 10-2009-0075529 |
| Nov. 18, 2009 | (KR) | 10-2009-0111710 |

(51) Int. Cl.
| G01N 33/574 | (2006.01) |
| A61K 31/00 | (2006.01) |
| C07K 14/00 | (2006.01) |
| A61K 31/10 | (2006.01) |
| A61K 31/122 | (2006.01) |
| C07C 317/44 | (2006.01) |
| C07C 323/52 | (2006.01) |

(52) U.S. Cl.
CPC ............ *G01N 33/5748* (2013.01); *A61K 31/10* (2013.01); *A61K 31/122* (2013.01); *C07C 317/44* (2013.01); *C07C 323/52* (2013.01); *C07C 2102/10* (2013.01)

(58) Field of Classification Search
None
See application file for complete search history.

(56) References Cited

U.S. PATENT DOCUMENTS

| 5,259,849 A | 11/1993 | Grollier et al. |
| 2005/0032794 A1 | 2/2005 | Padia et al. |
| 2010/0061973 A1* | 3/2010 | Sanchez-Garcia et al. .................. 424/130.1 |

FOREIGN PATENT DOCUMENTS

| CN | 1827578 | 9/2006 |
| JP | 61-033138 | 2/1986 |

OTHER PUBLICATIONS

Sun-Hye Lee et al. Neoplasia (New York, N.Y.) (Impact Factor: 5.48). Feb. 2009; 11(1):22-31.*
Downward (Nature Reviews; 3 pp. 11-22; 2003).*
Korean Intellectual Property Office, International Search Report for International Application No. PCT/KR2009/006896, Jul. 9, 2010.
Shen, Gui-Nan et al., "2-substituted thio- and amino-5,8-dimethoxy-1,4-naphthoquinones as a novel . . . ", Bulietin of the Korean Chemical Society, Jun. 2009, 30(6), 1416.
Gui-Nan Shen et al., "2-Substitiuted Thio- and Amino-5,8-dimethoxy-1,4-naphthoquinones as a Novel . . . ", Bulietin of the Korean Chem. Soc., 2009, pp. 1088-1092, vol. 30, No. 5.
Couladouros, E. A. et al., "Product class 3: naphtho-1,4-quinones", Science of Synthesis, 2006, pp. 217-322.
Rajeshwar P. Verma et al., "Elucidation of structure-activity relationships for 2- or 6-substituted . . . ", Bioorganic & Medicinal Chemistry, 2004, pp. 5997-6009.
Tapia, Ricardo A. et al., "Synthesis of furanonaphthazarin derivatives", Heterocycles, 1998, pp. 1365-1371.
Tandon et al., Bioorganic & Medicinal Chemistry Letters 14 (2004) 1079-1083.

* cited by examiner

*Primary Examiner* — Elly-Gerald Stoica
(74) *Attorney, Agent, or Firm* — Revolution IP, PLLC

(57) ABSTRACT

Provided are compounds for inhibiting Snail-p53 binding and therapeutic agents for cancer including the compounds as an effective component. The Snail-p53 binding inhibitors induce expression of p53 in K-Ras mutant cell lines, thereby enabling effective treatment or prevention of K-Ras mutant cancer, such as, pancreatic cancer, lung cancer, cholangioma, and colon cancer, of which diagnosis or treatment is not easy.

2 Claims, 23 Drawing Sheets

METHOD OF SCREENING OF THERAPEUTIC AGENTS FOR K-RAS MUTANT DRIVEN CANCERS

CROSS REFERENCE TO PRIOR APPLICATIONS

This application is a Divisional Application of U.S. patent application Ser. No. 13/130,159 filed on May 19, 2011 under 35 U.S.C. §120, which is a National Stage Patent Application of PCT International Patent Application No. PCT/KR2009/006896 filed on Nov. 23, 2009 under 35 U.S.C. §371, which claims priority to Korean Patent Application Nos. 10-2008-0116343 filed on Nov. 21, 2008, 10-2009-0018956 filed on Mar. 5, 2009, 10-2009-0075529 filed on Aug. 17, 2009, and 10-2009-0111710 filed on Nov. 18, 2009, which are all hereby incorporated by reference in their entirety.

SEQUENCE LISTING

An attached Sequence Listing is generated as i. name: 02280-1015_SEQ_CRF, ii. date of creation: Jan. 27, 2014, and iii. size: 5 KB in computer readable form (CRF).

BACKGROUND

The present invention is directed to a compound that inhibits SNAIL-p53 binding to induce expression of p53 so as to be effectively used in treating a K-Ras mutant cancer, such as pancreatic cancer, lung cancer, cholangioma, and colon cancer and a therapeutic agent for cancer including the compound as an effective component.

Improvement of anti-cancer drugs and diagnostic tools has raised 5 years survival rate of overall cancer patients up to 50%. However, some kinds of cancer including lung and pancreatic cancer still show extremely low survival rate, less than 10%. Accordingly, development of early diagnostic methods for these cancers is urgently needed to increase survival rates of the cancer patients. Interestingly, K-Ras is predominant event in such cancer, in particular, in pancreatic cancer of which survival rate is 5% or less.

Oncogenic Ras is known to induce senescence and apoptosis through p53 activation, and formation of an oncogenic Ras mediated tumor is assumed to occur under p53 deficient condition, and in particular, H-Ras induced cancer cells are suppressed by rapidly activated p53.

Currently available drugs for treating lung and pancreatic cancer have relatively weak effect on extension of life span, and cause various adverse effects. Accordingly, there is a need to develop a drug for effectively treating or early diagnosing such disease.

SUMMARY

The inventors of the present invention found that oncogenic K-Ras suppresses p53 by inducing SNAIL, identified that a compound can block an interaction between p53 and SNAIL, and found that the compound induces p53 expression in K-Ras mutant cell lines, thereby completing the present invention.

The present invention provides a method of screening a therapeutic agent for K-Ras mutant cancer, in which the method includes screening a candidate drug for inhibiting SNAIL-p53 binding.

The present invention also provides a compound for inhibiting SNAIL-p53 binding and a therapeutic agent for cancer including the compound as an effective component.

Also, the inventors of the present invention revealed that a particular region of p53, for example, a DNA binding domain has increasing permeation in K-Ras mutant cells, and thus, p53 can be used as a carrier to deliver drug specifically to K-Ras mutant cells. Also, they found that a K-Ras mutant cancer, such as pancreatic, lung, cholangiocarcinoma, and colon cancer, can be early diagnosed by detecting expression of SNAIL autoantibody, thereby completing the present invention Thus, the present invention also provides a drug delivery method for delivering drug specifically to K-Ras mutant cells by using endocytosis of a DNA binding domain of p53.

The present invention also provides a method of early diagnosing K-Ras mutant cancer by detecting expression of SNAIL autoantibody.

According to an aspect of the present invention, there is provided a method of screening a therapeutic agent for K-Ras mutant cancer, in which the method includes immobilizing p53 on to an ELISA plate and adding a SNAIL protein fragment to the plate having the immobilized p53, and screening a candidate drug that inhibits SNAIL-p53 binding by using an ELISA plate reader.

According to an aspect of the present invention, there is provided a compound represented by Formula 1 below or a salt thereof:

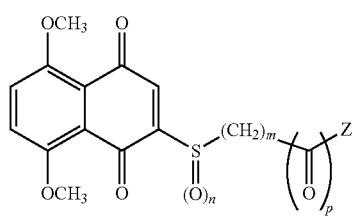

[Formula 1]

wherein in Formula 1,
m is an integer of 0 to 10, n and p each are 0 or 1,
Z is selected from the group consisting of —NH(CH$_2$)$_q$CH$_3$, —OH, a 4-phenylpiperidin group, a 4-phenylpiperazine group, an isobutylamino group, and an isobutyloxy group, and q is an integer of 0 to 9.

For example, the compound may be selected from the group consisting of 2-nonyl amino-5,8-dimethoxy-1,4-naphtoquinone; 2-decylamino-5,8-dimethoxy-1,4-naphtoquinone; 3-(5,8-dimethoxy-1,4-dioxonaphthalene-2-ylthio) propanoic acid; 11-(5,8-dimethoxy-1,4-dioxo-1,4-dihydronaphthalene-2-ylthio)undecanoic acid; isobutyl-11-(5,8-dimethoxy-1,4-dioxo-1,4-dihydroxynaphthalene-2-ylthio)-undecanoate; 11-(5,8-dimethoxy-1,4-dioxo-1,4-dihydronaphthalene-2-ylthio)-N-isobutyl undecanamide; and isobutyl 11-(5, 8-dimethoxy-1,4-dioxo-1,4-dihydronaphthalene-2-yl sulfinyl) undecanoate, or a salt thereof.

The compound of Formula 1 enables the method of screening a therapeutic agent for K-Ras mutant cancer to be used to selectively screen a drug for inhibiting SNAIL-p53 binding, thereby effectively treating or preventing K-Ras mutant cancer, such as pancreatic, lung, and colon cancer, that are difficult to be diagnosed or treated.

A method of screening a therapeutic agent for K-Ras mutant cancer according to the present invention enables a drug for inhibiting SNAIL-p53 binding, thereby effectively treating or preventing a K-Ras mutant cancer, such as pancreatic, lung, cholangiocarcinoma, and colon cancer.

Also, a DNA binding domain of p53 is used as a carrier to deliver drug specifically to K-Ras mutant cells, which is very useful for treatment of K-Ras mutant cancer. In addition, K-Ras mutant cancer may be early diagnosed through identification of expression of SNAIL autoantibody. Thus, it is possible to early diagnose pancreatic cancer of which diagnosis is difficult, thereby increasing a survival rate of cancer patients or treatment efficiency.

BRIEF DESCRIPTION OF DRAWINGS

FIG. 21 shows GST-full down assay results for identifying a SNAIL-p53 binding inhibiting effect of Nutlin-3 and compounds 5o and 7a.

DETAILED DESCRIPTION

Figure 1:
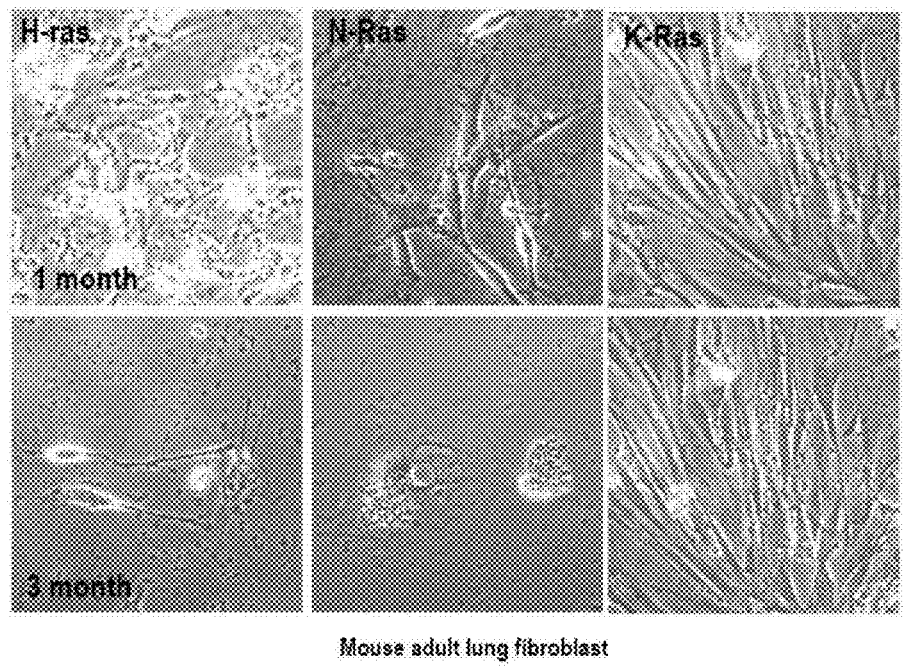
FIGS. 1, 2 and 3 show molecular mechanisms of SNAIL mediated p53 expression suppression.
Figure 1:
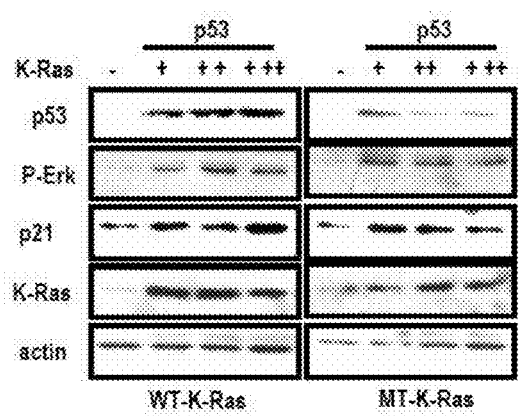
Figure 1:
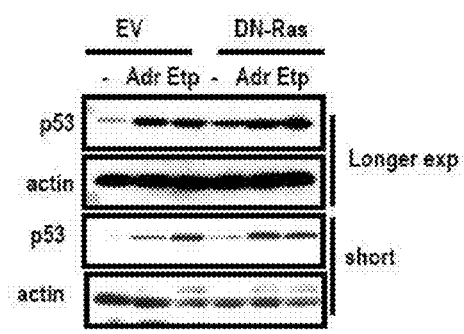

According to an embodiment, the compound of Formula 1 may be present in a form of a salt. The salt may be a pharmaceutically available salt of an inorganic acid, such as a hydrochloric acid or a sulfuric acid, or an organic acid, such as p-toluene sulfonic acid.

The compound of Formula 1 may be prepared through Reaction Schemes 1 to 5.

[Reaction Scheme 1]

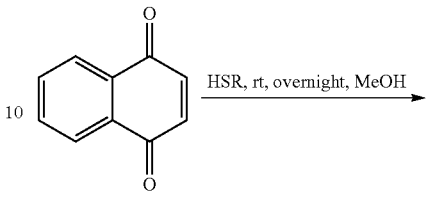

1

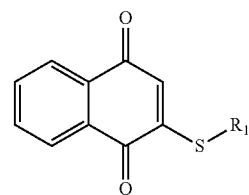

1-a: $R_1 = $ —$CH_3$   1-b: $R_1 = $ —$CH_2CH_3$
1-c: $R_1 = $ —$(CH_2)_2CH_3$   1-d: $R_1 = $ —$(CH_2)_3CH_3$
1-e: $R_1 = $ —$(CH_2)_4CH_3$   1-f: $R_1 = $ —$(CH_2)_5CH_3$
1-g: $R_1 = $ —$(CH_2)_6CH_3$   1-h: $R_1 = $ —$(CH_2)_7CH_3$
1-i: $R_1 = $ —$(CH_2)_8CH_3$   1-j: $R_1 = $ —$(CH_2)_9CH_3$

[Reaction Scheme 2]

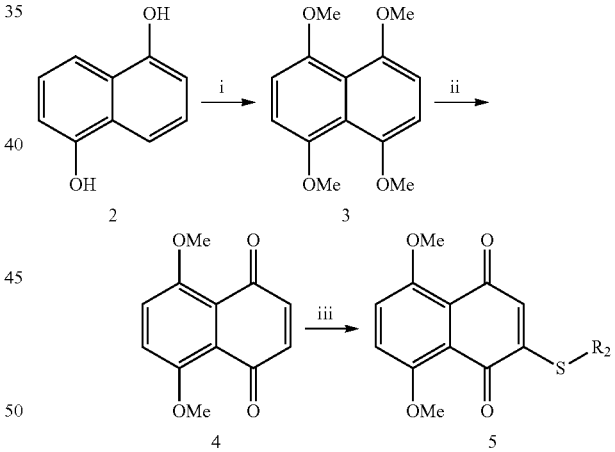

Reaction condition: (i) *Bulletin of the Chemical Society of Japan*, 60(1), 205~13, 1987

(ii) *Bulletin of the Chemical Society of Japan*, 61(6), 2039~45, 1988

(iii) $H_2NR$ or HSR, $Na_2Cr_2O_7$, $H_2SO_4$, rt, 4 h to overnight, MeOH 5-a: $R_2 = $ —$NHCH_3$   5-b: $R_2 = $ —$NHCH_2CH_3$
5-c: $R_2 = $ —$NH(CH_2)_2CH_3$   5-d: $R_2 = $ —$NH(CH_2)_3CH_3$
5-e: $R_2 = $ —$NH(CH_2)_4CH_3$   5-f: $R_2 = $ —$NH(CH_2)_5CH_3$
5-g: $R_2 = $ —$NH(CH_2)_6CH_3$   5-h: $R_2 = $ —$NH(CH_2)_7CH_3$
5-i: $R_2 = $ —$NH(CH_2)_8CH_3$   5-j: $R_2 = $ —$NH(CH_2)_9CH_3$
5-k: $R_2 = $ —$(CH_2)_2OH$   5-l: $R_2 = $ —$(CH_2)_3OH$
5-m: $R_2 = $ —$(CH_2)_4OH$   5-n: $R_2 = $ —$(CH_2)_6OH$
5-o: $R_2 = $ —$(CH_2)_2COOH$   5-p: $R_2 = $ —$(CH_2)_{10}COOH$

[Reaction Scheme 3]

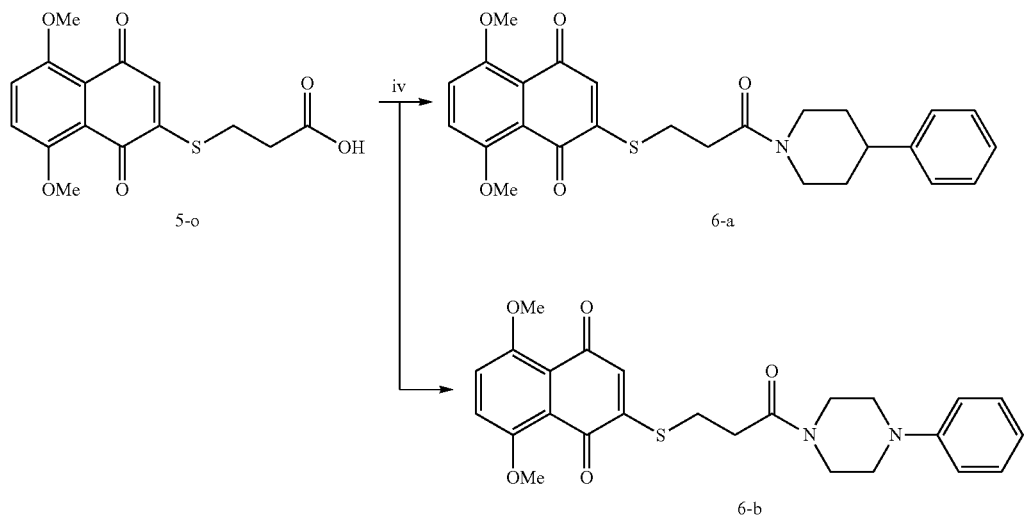

Reaction condition: (iv) EDC, 4-phenylpiperidine, rt, overnight, CHCl₃

[Reaction Scheme 4]

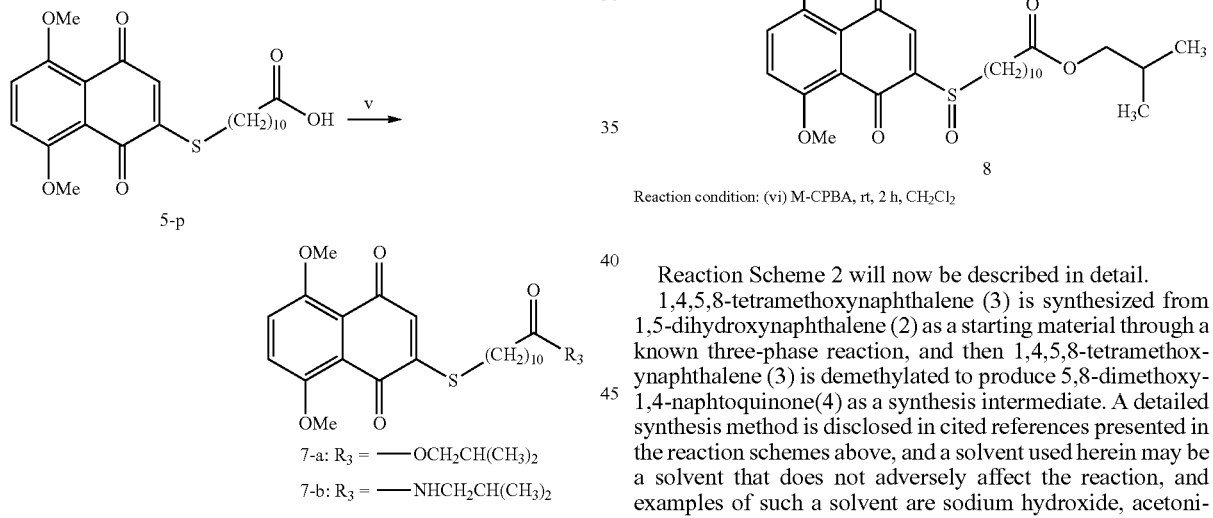

Reaction condition: (v) EDC, i-butylalcohol or i-butylamine, rt, overnight, CHCl₃

[Reaction Scheme 5]

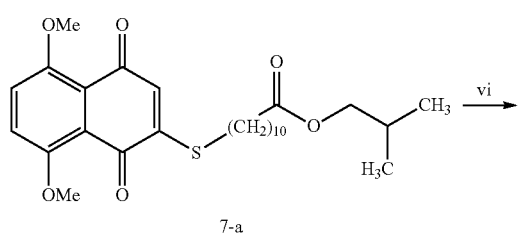

Reaction condition: (vi) M-CPBA, rt, 2 h, CH₂Cl₂

Reaction Scheme 2 will now be described in detail.

1,4,5,8-tetramethoxynaphthalene (3) is synthesized from 1,5-dihydroxynaphthalene (2) as a starting material through a known three-phase reaction, and then 1,4,5,8-tetramethoxynaphthalene (3) is demethylated to produce 5,8-dimethoxy-1,4-naphtoquinone(4) as a synthesis intermediate. A detailed synthesis method is disclosed in cited references presented in the reaction schemes above, and a solvent used herein may be a solvent that does not adversely affect the reaction, and examples of such a solvent are sodium hydroxide, acetonitrile, anhydrous methanol, N,N-dimethylformamide, and chloroform. The initial methylation is performed in such a manner that dimethyl sulfate is dropped to 1,5-dihydroxynaphthalene dissolved in sodium hydroxide in the presence of a nitrogen gas for 1 hour and the reaction was performed for 2 hours. The reaction product is re-crystallized with benzene to produce 1,5-dimethoxynaphthalene.

1,4,5,8-tetramethoxynaphthalene (3) is prepared by thermal-refluxing sodiummethoxide and iodine copper in dimethylformamide and methanol under an anhydrous condition for 30 hours. The refluxing is continued at reaction temperature of 80° C. or higher. Intermediate 5,8-dimethoxy-1,4-naphtoquinone is synthesized using nitric acid ceriumdiammonium. That is, nitric acid ceriumdiammonium is dropped thereto at room temperature for 30 hours and the reaction is further performed for 30 minutes. In order to prepare compounds 5a to 5p, intermediate 5,8-dimethoxy-1,4-naphtoquinone(4) is dissolved in methanol, and desired amine or mercaptan or a mercaptan having an end to which a carboxylic group or a hydroxyl group is bound is added thereto and stirred at room temperature for 4 hours overnight, and a reaction progress is identified by TLC and the reaction is worked-up by using sulfuric acid and dichromate sodium aqueous solution, and the reaction product is isolated by silicagel column chromatography.

When a 4-phenylpiperidine or 4-phenylpiperazine derivative is attached to a carboxylic group at site 2 of compound 5o in the following step, N-(3-dimethylaminopropyl)-N-ethyl-carbodiimide hydro chloride (EDC), instead of 1,3-dicyclohexylcarbodiimide (DCC) and N,N-dimethylaminopyridine (DMAP), is added thereto to synthesize compounds 6a and 6b, and in this case, the reaction yield is high and in a separation process, the reaction product is clearly separated without urea. In the next step, when isobutylalcohol and isobutylamine are attached by using compound 5p, compounds 7a and 7b may be easily obtained by using N-(3-dimethylaminopropyl)-N-ethylcarbodiimidehydrochloride (EDC). When sulfoxide compound 8 is synthesized, compound 7a and MCPBA are used and a reaction progress is identified by TLC. The reaction is worked-up by using sodium bicarbonate, and the reaction product was passed through a silicagel column to obtain purified compound 7a.

However, the methods according to Reaction Schemes 2 to 5 are just an example of a method of preparing the compound of Formula 1. For example, reaction conditions, such as an amount of a reaction solvent used, an amount of a base used, and an amount of a reaction material used, are not limited thereto, and various other synthesis methods that are known to one of ordinary skill in the art, in addition to the methods according to Reaction Scheme 2 to 5, may also be used to prepare the compound of Formula 1.

Also, the present invention provides a therapeutic agent for cancer that includes a compound for inhibiting SNAIL-p53 binding as an effective component.

The compound may be a compound of Formula 1 or a salt thereof, and preferably, a compound selected from the group consisting of 2-nonylamino-5,8-dimethoxy-1,4-naphtoquinone; 2-decylamino-5, 8-dimethoxy-1,4-naphtoquinone; 3-(5, 8-dimethoxy-1,4-dioxo-naphthalene-2-ylthio)propanoic acid; 11-(5,8-dimethoxy-1,4-dioxo-naphthalene-2-ylthio)undecanoic acid; isobutyl-11-(5, 8-dimethoxy-1,4-dioxo-1,4-dihydronaphthalene-2-ylthio)-undecanoate; 11-(5, 8-dimethoxy-1,4-dioxo-1,4-dihydronaphthalene-2-ylthio)-N-isobutyl undecanamide; and isobutyl 11-(5,8-dimethoxy-1,4-dioxo-1,4-dihydronaphthalene-2-ylsulfinyl) undecanoate, or a salt thereof.

The cancer may be K-Ras mutant cancer. For example, the cancer may be selected from the group consisting of pancreatic cancer, lung cancer, cholangioma, and colon cancer.

The therapeutic agent for cancer according to the present invention may further include a carrier, an excipient, or a diluting agent, each of which is appropriate for use as a therapeutic agent and is conventionally used in preparing a pharmaceutical composition.

Examples of a carrier, an excipient, and a diluting agent which are available for the present invention are lactose, dextrose, sucrose, sorbitol, mannitol, xylitol, erythritol, maltitol, amylum, acacia rubber, alginate, gelatin, calcium phosphate, calcium silicate, cellulose, methyl cellulose, microcrystalline cellulose, polyvinylidon, water, methylhydroxybenzoate, propylhydroxybenzoate, magnesium stearate, and mineral oil.

The therapeutic agent for cancer may be prepared in an oral formation, such as powder, a granule, a tablet, a capsule, a suspension, an emulsion, a syrup, or an aerosol, an external applicable formulation, an suppository formulation, or a sterile injectable solution, according to a corresponding conventional preparation method.

The preparation may be performed using a conventional diluting agent or excipient, such as a filling agent, an extender, a binder, a wetting agent, a disintegrant, or a surfactant. Examples of a solid formulation for oral administration are a tablet, a pill, powder, a granule, and a capsule, and such solid formulations are prepared by mixing the compound as described above with one or more excipients, for example, amylum, calcium carbonate, sucrose or lactose, or gelatin.

Also, in addition to the excipients, a lubricant, such as magnesium stearate, or talc, may additionally be used. Examples of a liquid formulation for oral administration are a suspension, a preparation dissolved in liquid, an emulsion, and syrup. The liquid preparation may include, in addition to a conventional simple diluting agent, such as water or liquid paraffin, various other excipients including a wetting agent, a sweetener, an odorant, and a preservative.

Examples of a formulation for parenteral administration are a sterile aqueous solution, a non-aqueous solvent, a suspension, an emulsion, a lyophilization formulation, and a suppository formulation. Examples of a non-aqueous solvent and a suspension are vegetable oil, such as propylene glycol, polyethylene glycol, or olive oil, and an injectable ester such as ethylollate. As a support for suppositories, witepsol, macrogol, tween 61, Cacao oil, laurin oil, or glycerogeratin may be used.

A dose of the therapeutic agent for cancer may differ according to the age, gender, or weight of a patient, and for example, a dose of 0.1 to 100 mg/kg may be administered as a bolus or divided into a few portions per day.

In addition, the dose of the therapeutic agent for cancer may be increased or decreased according to an administration pathway, a progress degree of disease, a gender, a weight, or an age. Accordingly, the dose may not limit the scope of the present invention in any respects.

The therapeutic agent for cancer may be administered to a mammal, such as rats, mice, livestock, or humans, through various administration pathways. All administration methods may be obvious, for example, oral administration, rectal administration, or intravenous, intramuscular, hypodermic, intrauterine epidural, or intracerebroventricular injection.

Also, the present invention provides a K-Ras mutant cells-specific drug delivery method of delivering a target drug specifically to K-Ras mutant cells by endocytosis of a DNA binding domain of p53.

The DNA binding domain includes a sequence of 90-280 of human p53 amino acid sequence (Genbank Accession No. P04637).

Preferably, the drug delivery method may include treating cells with a DNA binding domain of p53 and a target drug; and delivering the target drug to neighboring K-Ras mutant cells by endocytosis of the DNA binding domain of p53.

Also, the present invention provides a method of early diagnosing a K-Ras mutant cancer by detecting SNAIL antibody expression.

The SNAIL antibody expression may be detected in a serum of a patient having K-Ras mutant cancer, and the K-Ras mutant cancer may be cancer selected from the group consisting of pancreatic cancer, lung cancer, cholangioma, and colon cancer.

Preferred embodiments of the present invention will now be described in detail. However, the embodiments are presented only for illustration purposes.

Molecular Mechanism of SNAIL Mediated p53 Suppression

Example 1

1. Isolation of Mouse Fibroblast and Immortalization 6 month-old male mouse was scarified to collect lung fibroblast. After isolation, the lung tissue was chopped and dissociated using a culture-mess. After three-day of incubation in DMEM medium containing 20% FBS, attached cells were seeded in culture dishes and transfected with mutant H-Ras, N-Ras, and K-Ras using Jetpei. After 72 hours, the transfected cells were selected using 400 μg/ml of G418 containing DMEM.

2. Cell Culture and Reagents Preparation

Cell lines used herein were obtained from ATCC and maintained in RPMI-1640 or DMEM containing 10% FBS. Antibodies used herein were purchased from Santa Cruz or Cell Signaling (p53-R, p-Erk). Ras expression vectors and SNAIL vectors were provided by Dr. Chi SG and Hung M-C respectively. Chemicals used herein were purchased from Calbiochem. Recombinant p53 was obtained from Assay designs.

Cell fraction analysis was performed using a Subcell fraction Kit (Merck) according to the manufacturer's protocol. For analysis of media, a cell cultured media was collected and concentrated by using Centricon (Millipore) or EtOH precipitation.

3. Immuno-Staining and Western Blotting

For cell staining, the cultured cells were washed and fixed with 100% Me-OH and incubated with antibodies (First antibody: 1: 200, overnight at 4° C.; secondary antibody: 1: 1000, 2 hours at RT). To detect secreted p53 and SNAIL, HCT116 p53$^{-/-}$ cells were transfected with vectors for 24 hours in 1 ml PRMI 1640 medium and fixed by adding of 1 ml of 2% PFA without washing. After fixation, cells were washed with PBS twice and incubated with blocking buffer (PBS+anti-Human antibody (1: 500)) to eliminate non-specific binding. After washing with PBS, cells were incubated with anti-p53 and anti-SNAIL antibodies and matched with the secondary antibody. For protein analysis, protein was extracted through RIPA buffer and the sample was applied to SDS-PAGE according to a conventional western blot protocol.

Immuno-precipitation analysis was performed according to a conventional protocol. That is, cell lysate was initially incubated with an antibody for 4 hours and then incubated with protein-A/G-agarose for 2 hours. The incubation product was centrifuged and washed 3 times. SDS-PAGE/WB analysis was performed using the precipitated complex.

4. Transfection and Reviewing of si-RNA Effect

Jetpei was performed for cell transfection according to the manufacturer's protocol. Cells were incubated with DNA/Jetpei mixture for 24 hours in a complete media. In order to knock out in vitro gene, si-RNA for SNAIL and MDM2 were prepared. The si-RNA was transfected using Jetpei, and after 24 hours, the effect was checked.

5. Experimental Results

As shown in FIG. 1A, the transfection of N-Ras or H-Ras induced apoptosis or senescence, but K-Ras transfected cells were growing and maintained even over than 6 months from the transfection of K-Ras.

Figure 2:
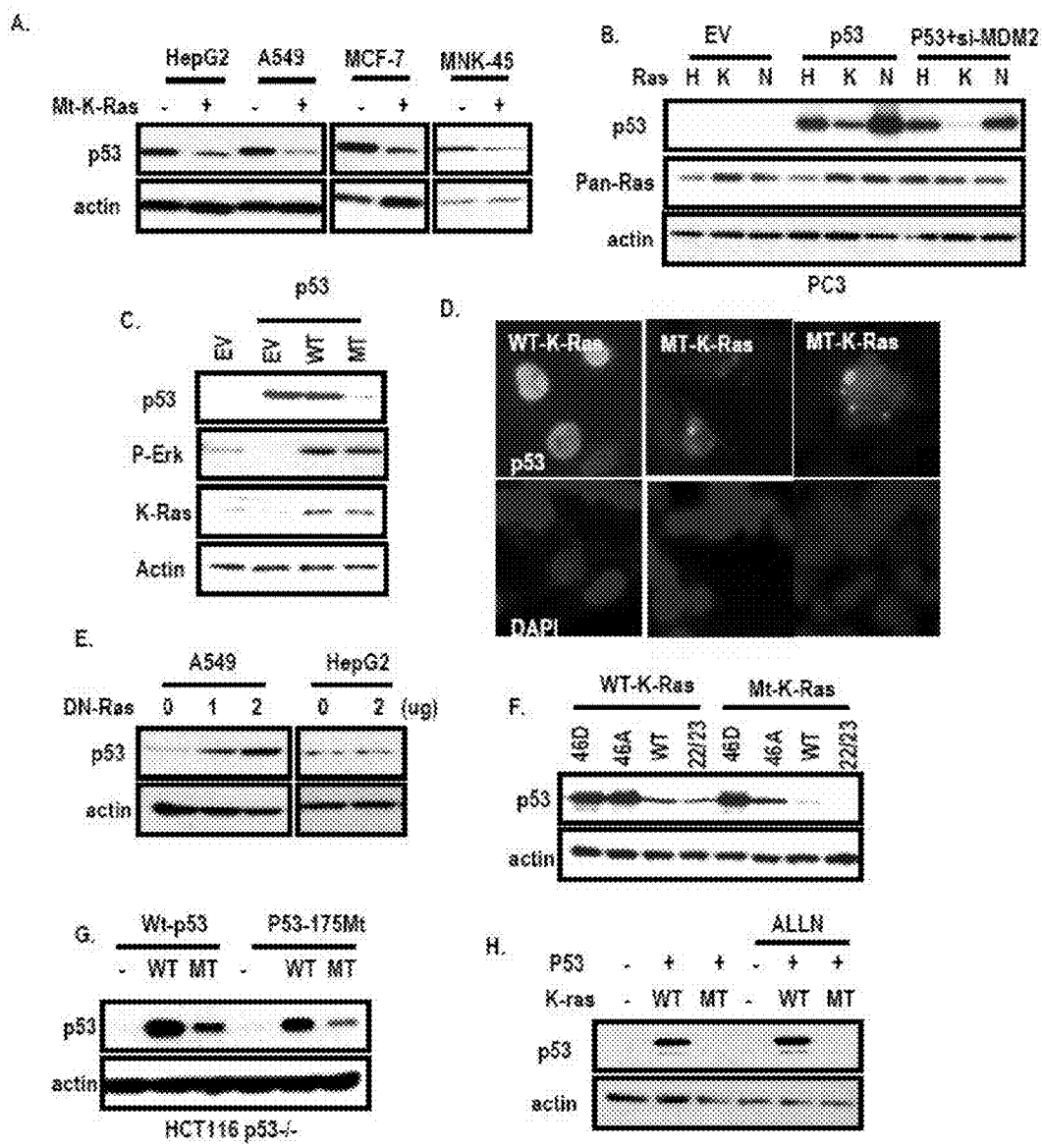

Also, Forced expression of oncogenic K-Ras suppressed the p53 expression in wild type p53-containing cell lines (see FIG. 2A), and differentially from H-Ras or N-Ras, K-Ras evoked p53 suppression, which was not blocked by si-MDM2 (see FIG. 2B). However, wild type K-Ras did not suppress the p53 expression (see FIGS. 2C and 2D).

As shown in FIG. 1B, p53 was suppressed as in a K-Ras-dose dependent manner. Blocking of Ras activity though DN-Ras increased the p53 expression only in K-Ras mutated A549 but not in HepG2 (FIG. 2E).

This result suggests that endogenous oncogenic K-ras suppresses p53 expression. However, as shown in FIG. 1C, DN-Ras did not show clear synergic effects on DNA damage-mediated p53 suppression. This shows that strong genotoxic stress overcame the oncogenic K-Ras-mediated p53 suppression.

As shown in FIGS. 2F and 2G, K-Ras-mediated p53 suppression was detected in point mutant. However, p53 S46D which is an active form of p53 showed the resistance to K-Ras-mediated p53 suppression. This result is consistent with the previous result that genotoxin induced p53 activation which overcame K-Ras-mediated suppression.

Since 22/23 mutant does not associate with MDM2, it was confirm that K-ras-mediated p53 suppression is achieved through MDM2 independent pathway. Also, since proteasome-inhibitors did not block the K-Ras-mediated p53, there is irrelevance of MDM2 or p53 ubiquintin system (see FIGS. 1A and 2H).

Also, the effect of MAPK signaling inhibitors on K-Ras-mediated p53 suppression showed that blocking of MAPK pathway did not abolish the effect on K-Ras-mediated p53 suppression. These results implied that K-Ras mediated p53 suppression would be achieved through novel pathway.

Figure 12:
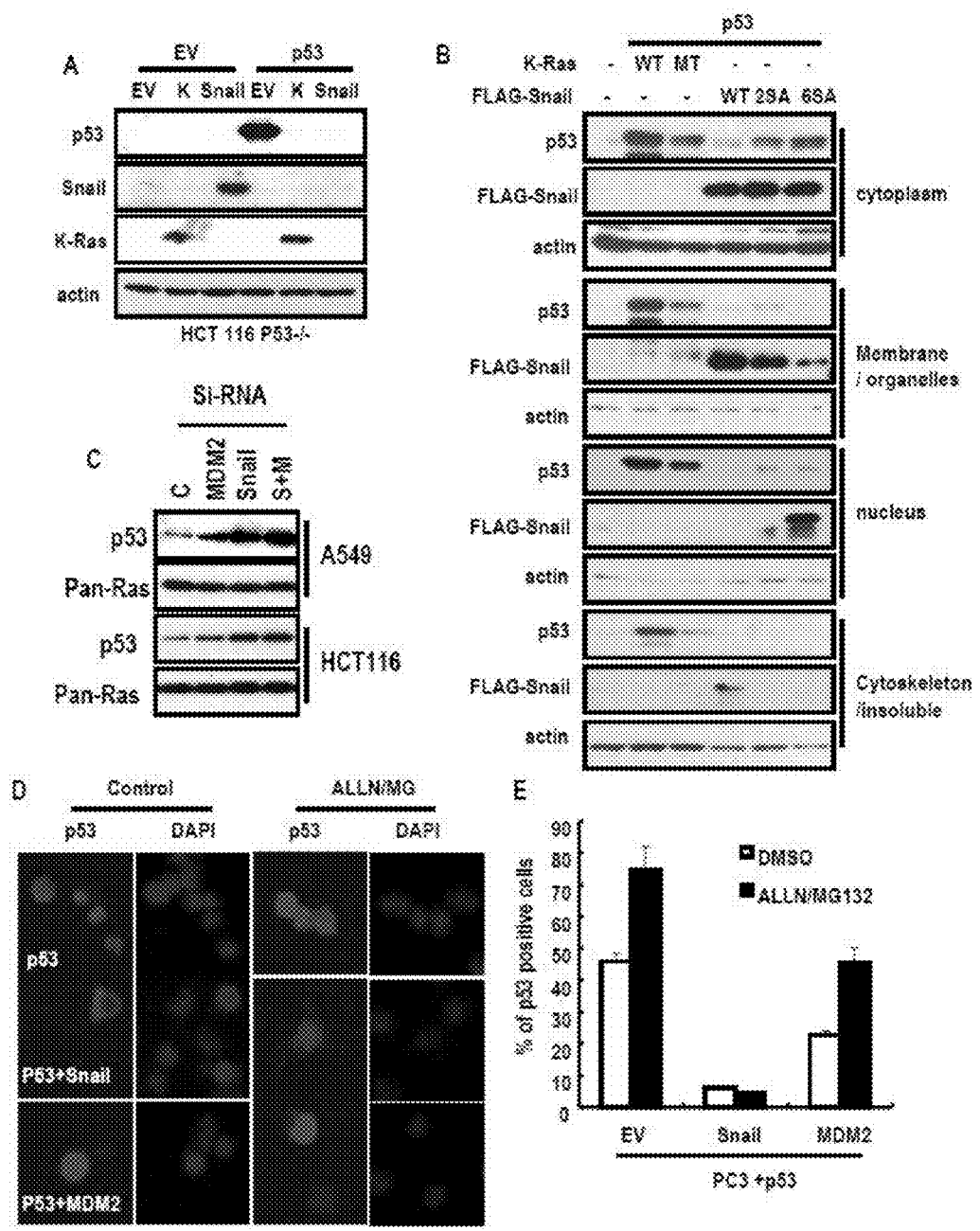
FIG. 12 shows molecular mechanisms of SNAIL mediated p53 expression suppression.

Also, distribution of p53 by SNAIL in an insoluble fraction showed that as shown in FIG. 12A, p53 was reduced by SNAIL or oncogenic K-Ras. By dividing cells into 4 fractions, such as, nuclear, cytoplasmic, membrane/organells, and insoluble fractions, it was found that as shown in FIG. 12B, p53 which was reduced by SNAIL; was not recovered in any kinds of subcellular fractions.

Also, elimination of SNAIL from K-Ras mutant cells induced p53 dominantly than si-MDM2 (FIG. 12C). And, as shown in FIGS. 12D and 12E, differentially from MDM2-mediated suppression, reduction of p53 by SNAIL was not recovered by proteasome inhibitors.

Example 2

1. Western Blot and In Vitro Kinase or Binding Assay

To examine direct binding between SNAIL and p53, a membrane was loaded with recombinant p53 or SNAIL or p53 transfected cell lysate through typical SDS-PAGE and gel transfer method. After blocking with 5% non-fat dry milk, the membrane was incubated with p53 or SNAIL transfected p53$^{-/-}$ HCT116 cell lysate for 4 hours at 4° C. After washing, the membrane was treated with a WB procedure by using p53 antibody or SNAIL antibody.

For in vitro binding, the recombinant p53 and GST-SNAIL were alternately incubated for 1 hour at 4° C. and performed the IP with p53 antibody or GST antibody and WB with GST or p53 antibody. To examine the modification of SNAIL, 293 cells were used for transfection. After fraction or lysis, lysates were incubated with GST or GST-SNAIL for 1 hour at 25° C.

and subjected into SDS-PAGE and WB analysis. Antibodies for p-MAPK substrate and p-ATM/ATR substrate were obtained from cell signaling.

2. Experimental Results

Figure 3:
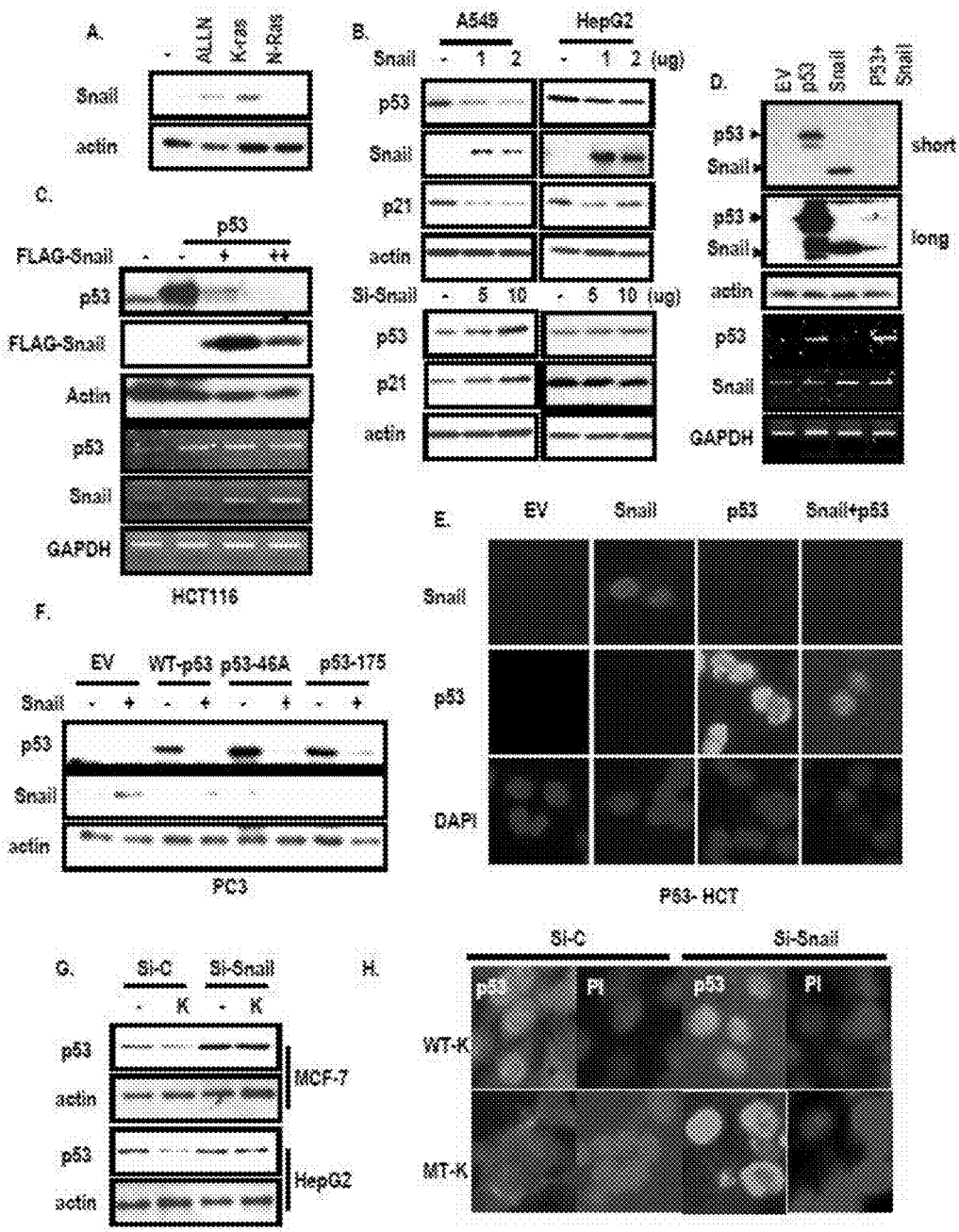

As shown in FIG. 3A, the effect of K-Ras on SNAIL expression was checked and it was found that SNAIL was induced by K-Ras. Also, the effect of SNAIL on p53 expression in cell lines was checked and it was found that as shown in FIG. 3B, overexpression of SNAIL suppressed p53 in A549 and HepG2 cell lines, whereas SNAIL knock down induced p53 only in A549 (oncogenic K-Ras containing cell line) but not HepG2.

Figure 4:
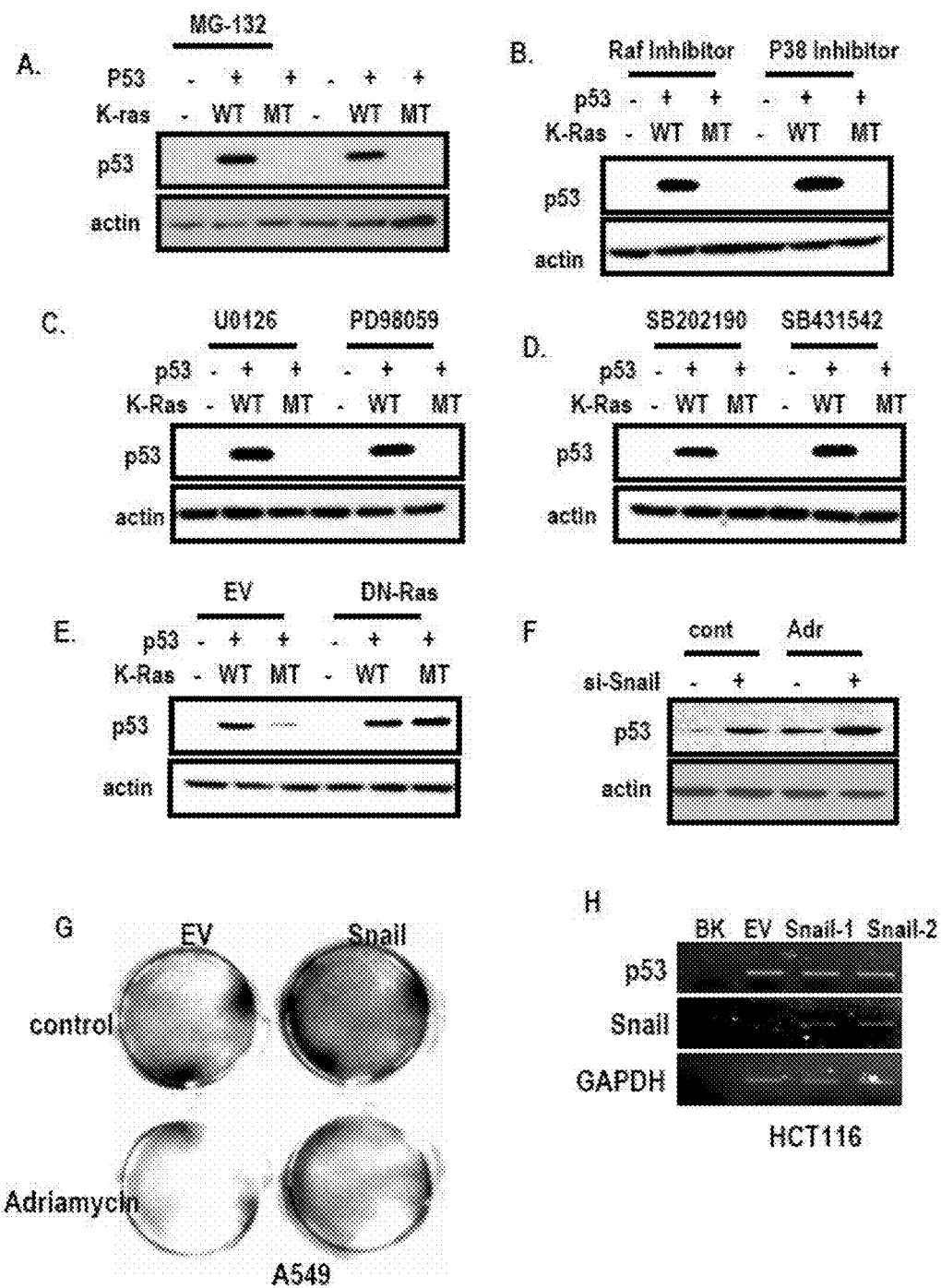
FIG. 4 shows that oncogenic K-Ras mediated p53 suppression is not blocked by a chemical inhibitor.

In addition, si-SNAIL increased the sensitivity to a DNA damage agent (see FIG. 4F). Thus overexpression of SNAIL promoted cell proliferation and render the resistance to DNA-damage-induced cell death (see FIG. 4G).

As shown in FIG. 3C, SNAIL also suppressed the exo-p53 as well as endo-p53, similarly to K-Ras (FIG. 2C). When SNAIL and p53 were co-transfected as shown in FIGS. 3C and 3D, they were reduced together, in regardless of mutant p53. However, mRNA of SNAIL and p53 were not reduced (FIGS. 3C and 3D). Also, the effect of SNAIL on p53 transcript showed that SNAIL did not reduce p53 mRNA (FIG. 4H).

Accordingly, these results indicated that although p53 and SNAIL were well-confirmed transcriptional regulators, their reduction was irrelevance with transcriptional regulation. In addition, elimination of SNAIL blocked the K-Ras-mediated p53 suppression as shown in FIGS. 3G and 3H. Also, the similar result was obtained from exo-p53. These results indicate that K-Ras-mediated p53 suppression is achieved through SNAIL induction.

Figure 5:
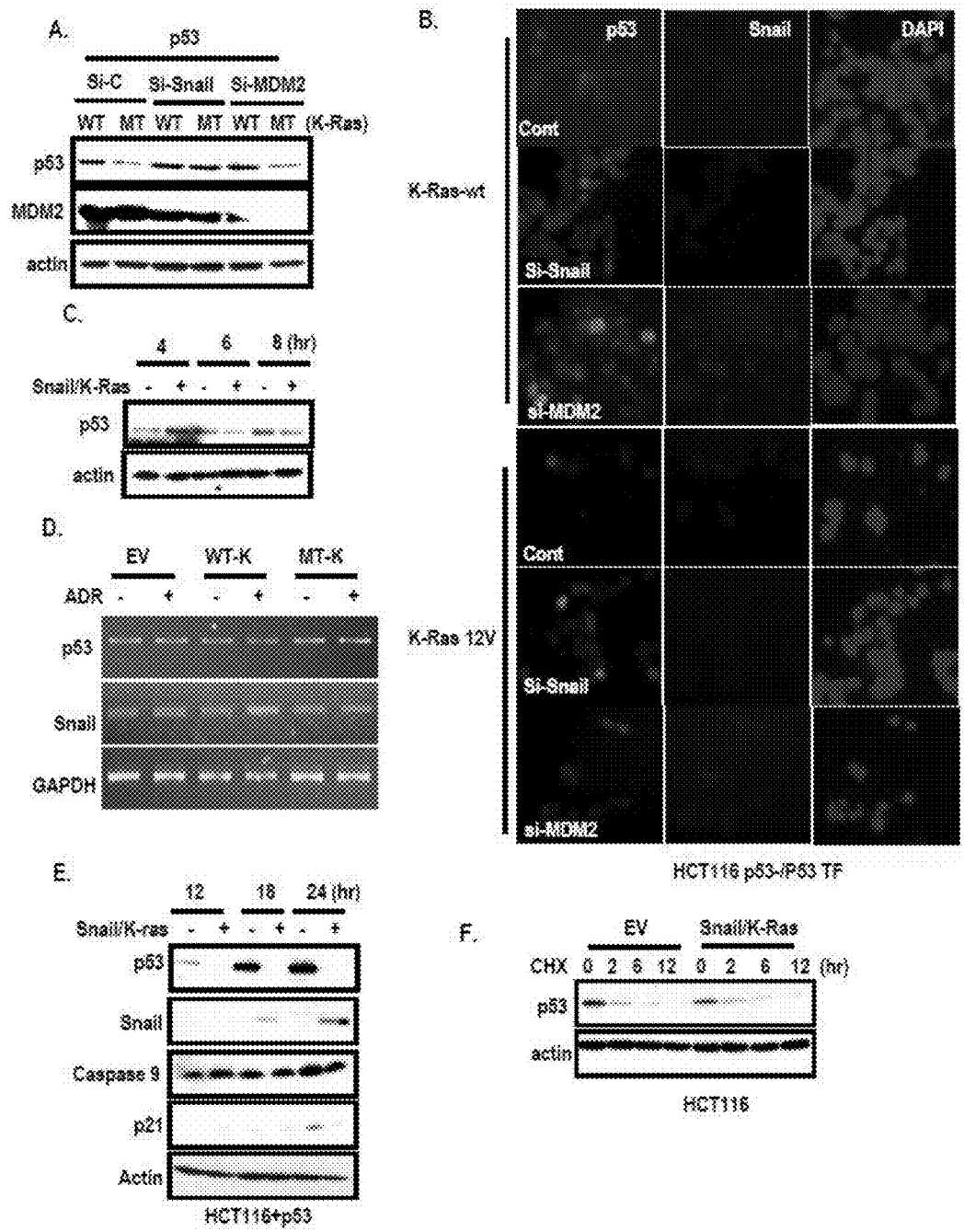
FIG. 5 shows that SNAIL is a critical mediator for oncogenic K-Ras mediated p53 suppression.

Also, as shown in FIG. 5C, oncogenic K-Ras induced p53 within 4 hours, whereas p53 was reduced after 6 hours. This result indicated that p53 suppression was not achieved by transfection-artifact but an effect of transfected proteins.

Also, as shown in FIG. 5E, apoptosis and cell cycle in KRas/SNAIL transfected cells were checked, and it was found that apoptosis and cell cycle inhibition was not obviously induced by K-Ras/SNAIL.

Also, the reduction of p53 by K-Ras/SNAIL in Aphidicolin treated cells was observed. This result suggested that reduction of p53 was not linked to cell cycle.

Also, the effect of SNAIL on half-life of p53 through CHX-pulse chase was checked, and it was found that as shown in FIG. 5F, SNAIL did not shorten p53 half-life. In addition, the effect of SNAIL on the expression of p53 S46D was checked and it was found that, as shown in FIG. 6A, differentially from K-Ras, SNAIL suppressed p53 S46D expression.

Figure 6:
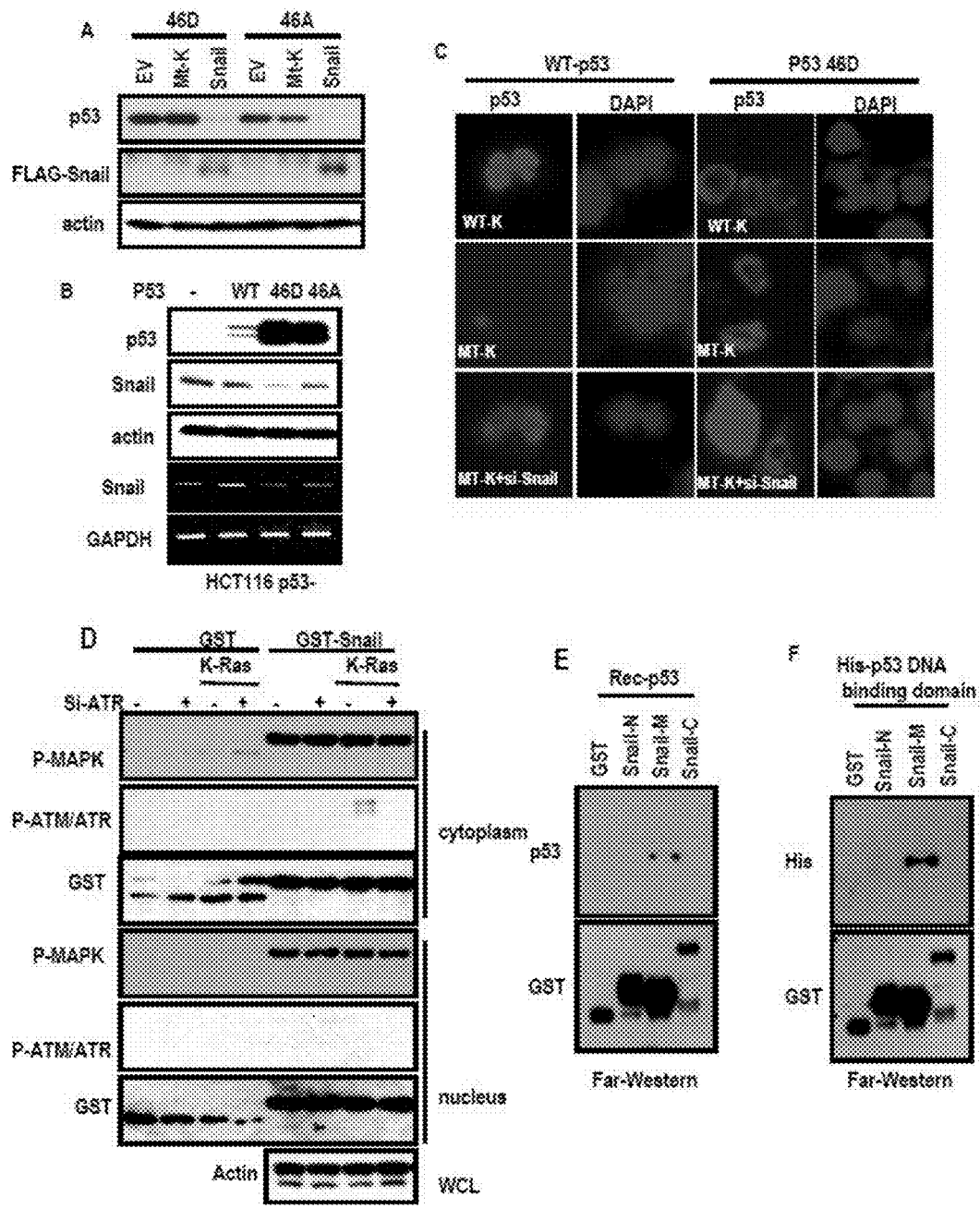
FIG. 6 shows a direct interaction between SNAIL and p53.

Also, the effect of p53 S46D on SNAIL expression was checked and it was found that, as shown in FIG. 6B, S46D suppressed SNAIL expression at transcription and translation levels. Accordingly, differentially from wild type p53 in which si-SNAIL restored the p53 suppression, as shown in FIG. 6C, si-SNAIL did not induce p53 expression when S46D was transfected.

These results indicate that under certain stress condition, activated p53 by modification at serine 46 residue may overcome K-Ras mediated suppression.

Also, induction of SNAIL was achieved through ATR.

To address how K-ras induce SNAIL, the engagement of AKT was examined. It was known that Ras activates AKT to suppress GSK-3-mediated SNAIL destabilization.

Figure 7:
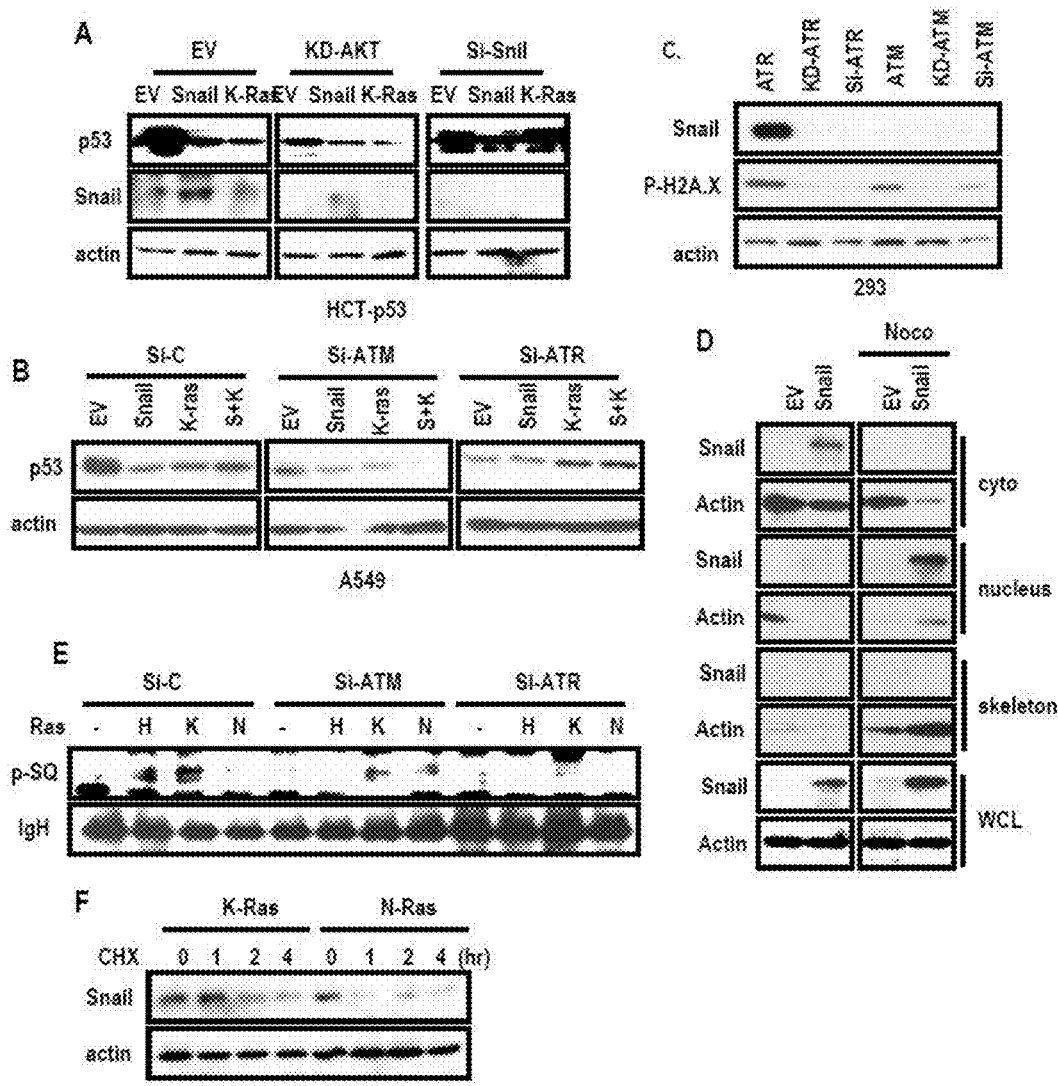
FIG. 7 shows conditions required to activate ATR in stabilizing K-Ras induced SNAIL.

But AKT-KD did not block the SNAIL or K-Ras-induced p53 suppression as shown in FIG. 7A. In contrast, suppression of ATR through si-RNA blocked the p53 suppression as shown in FIG. 7B. Indeed, SNAIL was increased by ATR but not ATM and nocodazole treatment as shown in FIGS. 7C and 7D. In vitro kinase assay showed that SNAIL was phosphorylated by ATR as shown in FIG. 6D. K-Ras, which has been known to activate ATR, also increased p-SNAIL as in ATR-dependent manner as shown in FIG. 7E and extended half-life of SNAIL.

Example 3

1. Recombinant Proteins and GST-Pull Down Analysis

Three human SNAIL fragments (residues 1-90, 91-112, and 113-264) and p53 fragments (1-93 and 93-292) were expressed in *Escherichia coli* (*E. coli*) as a GST-fusion protein. Each of the fragments was loaded on to GSH-agarose, washed, and then eluted using a buffer containing 20 mM reduced glutathione. The eluted fractions were further purified using an anionexchange chromatography (HitrapQ). The recombinant human p53 protein (residues 94 292) was expressed in *E. coli* using a vector pET28A which contains a hexa-histidine tag at C terminus.

The p53 protein was purified using Ni-NTA affinity and size exclusion chromatography (Superdex 200). To identify a direct binding between p53 and SNAIL, agarose bead conjugated GST or GST-SNAIL was incubated with cell lysate or His-p53 in RIPA for 45 min at 4° C. After washing with PBS and RIPA, precipitated protein was subjected into SDS PAGE and WB.

2. Experimental Results

Figure 8:
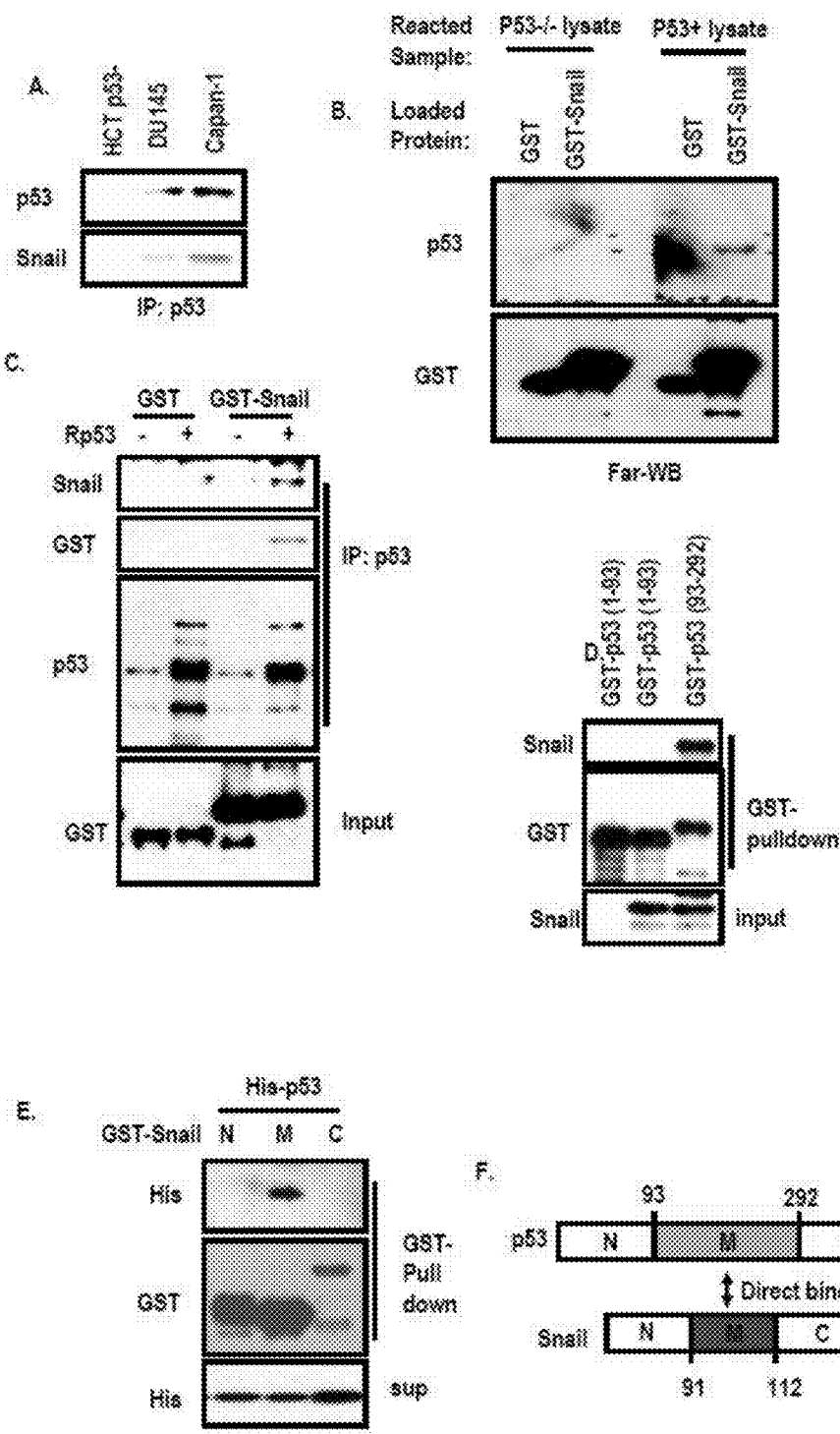
FIG. 8 shows a direct binding between SNAIL and p53.

Since SNAIL is nuclear protein, both of SNAIL and p53 were disappeared when they were co-transfected together (see FIGS. 3D to 3F). As shown in FIG. 8A, it was confirmed from endo-IP that these proteins are associated with each other. As shown in FIGS. 8B and 8C, far-western blot analysis and GST-Pull down assay indicated that SNAIL and p53 were directly interacted with each other. Also, a DNA binding domain of p53 and a middle region of SNAIL performed as a binding domain (see FIGS. 8D to 8F, 6E, and 6F.)

Example 4

1. Preparation of ELISA System for Chemical Screening

To isolate SNAIL-p53 binding inhibitor, ELISA system was prepared. His-p53 (93-292) was immobilized on 96 well plates using 0.5 PFA. After drying and washing, the 96 well plates were incubated with GST SNAIL with 0.1 μM of chemicals (final concentration). After 1 hour incubation, the 96 well plates were washed with TBST and incubated with anti-GST-antibody (1: 10000, 45 min) and anti-mouse-IgG-HRP (1; 50000, 30 min). After washing twice, plates were incubated with a TMB solution and a stop solution. Measurement was performed using an ELISA plate reader.

2. Experimental Results

Figure 9:
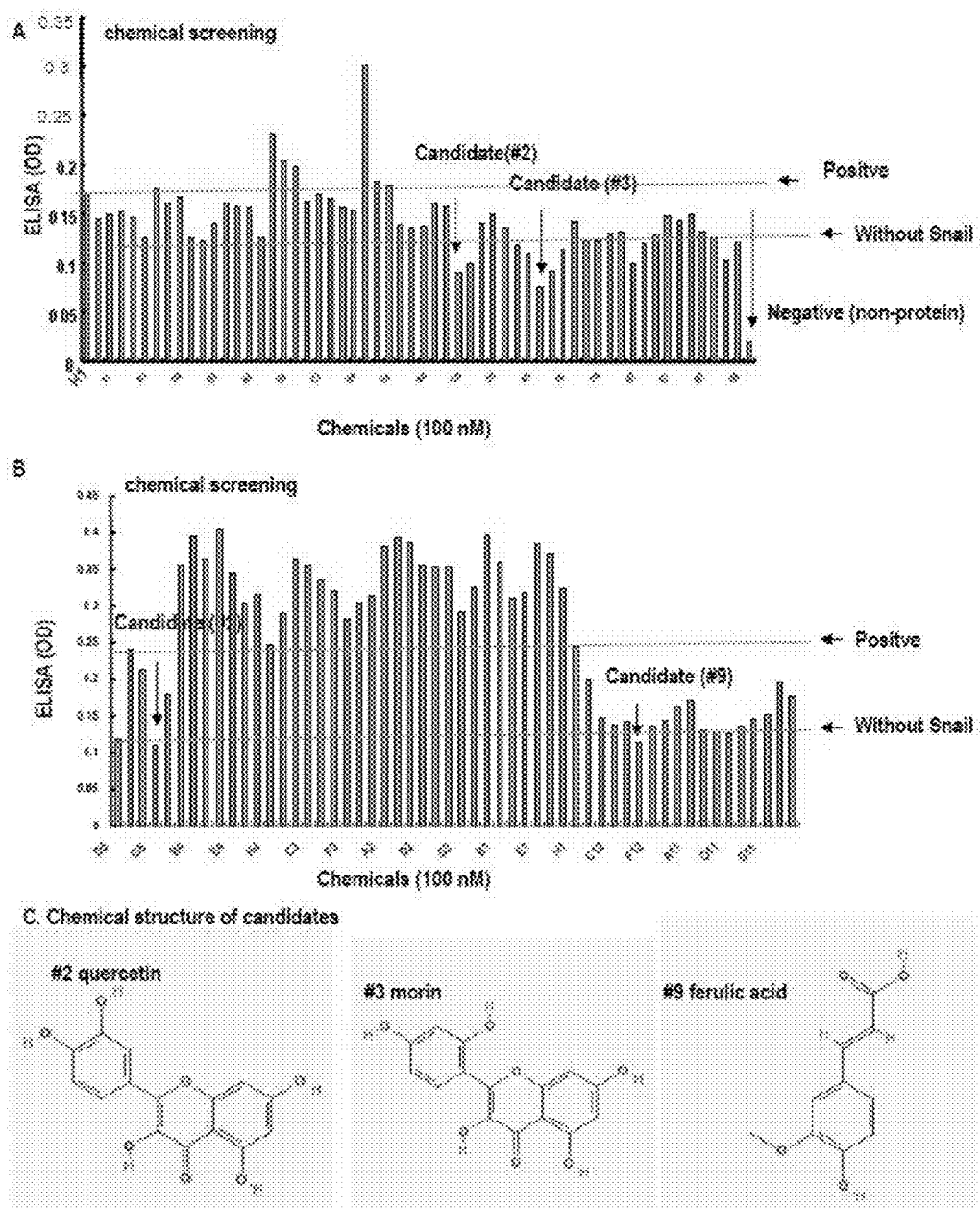
FIG. 9 shows identification of a SNAIL and p53 binding inhibitor.
Figure 10:
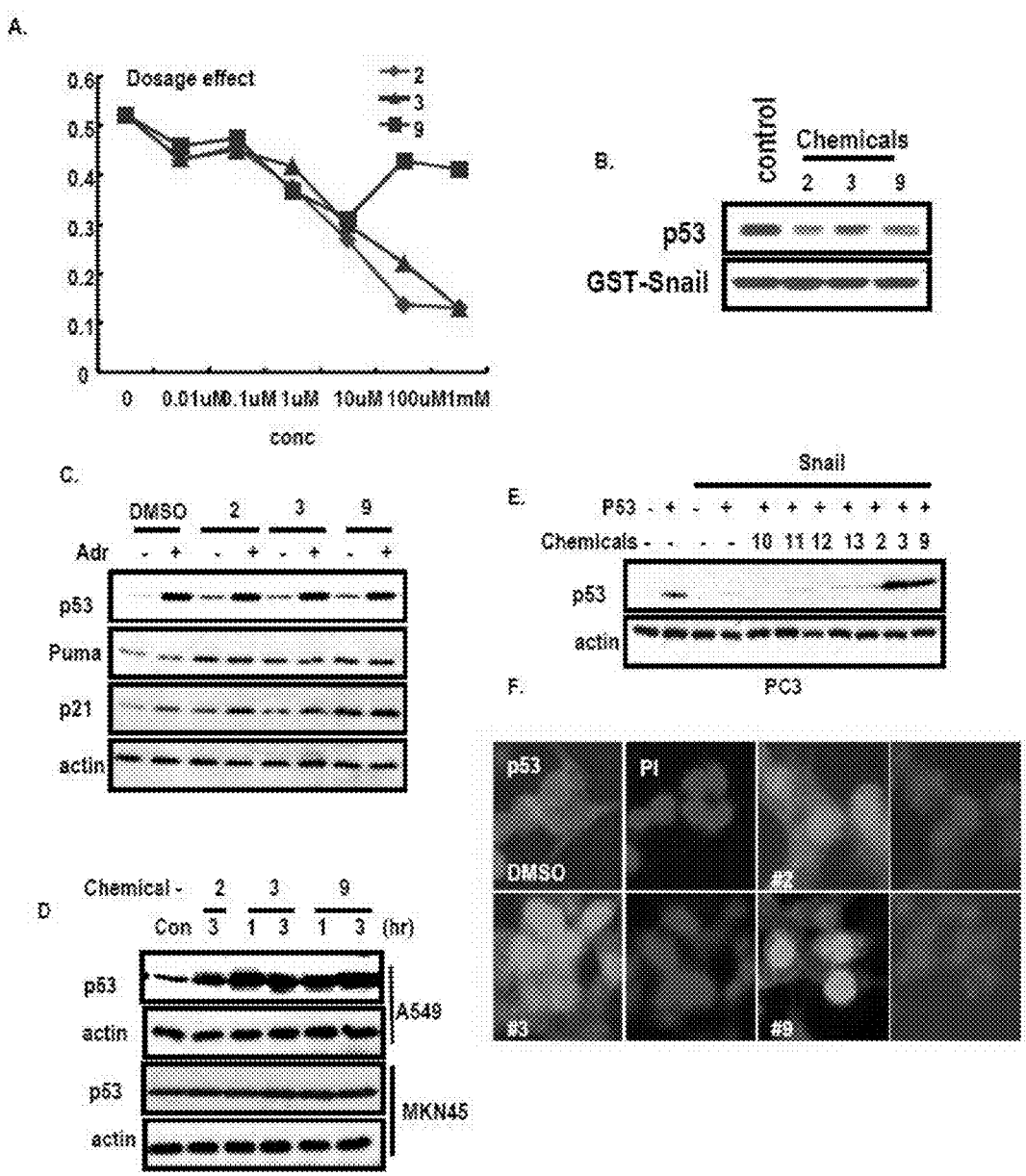
FIGS. 10 and 11 show that p53 function is induced in K-Ras mutant cells by blocking SNAIL and p53 binding.
Figure 11:
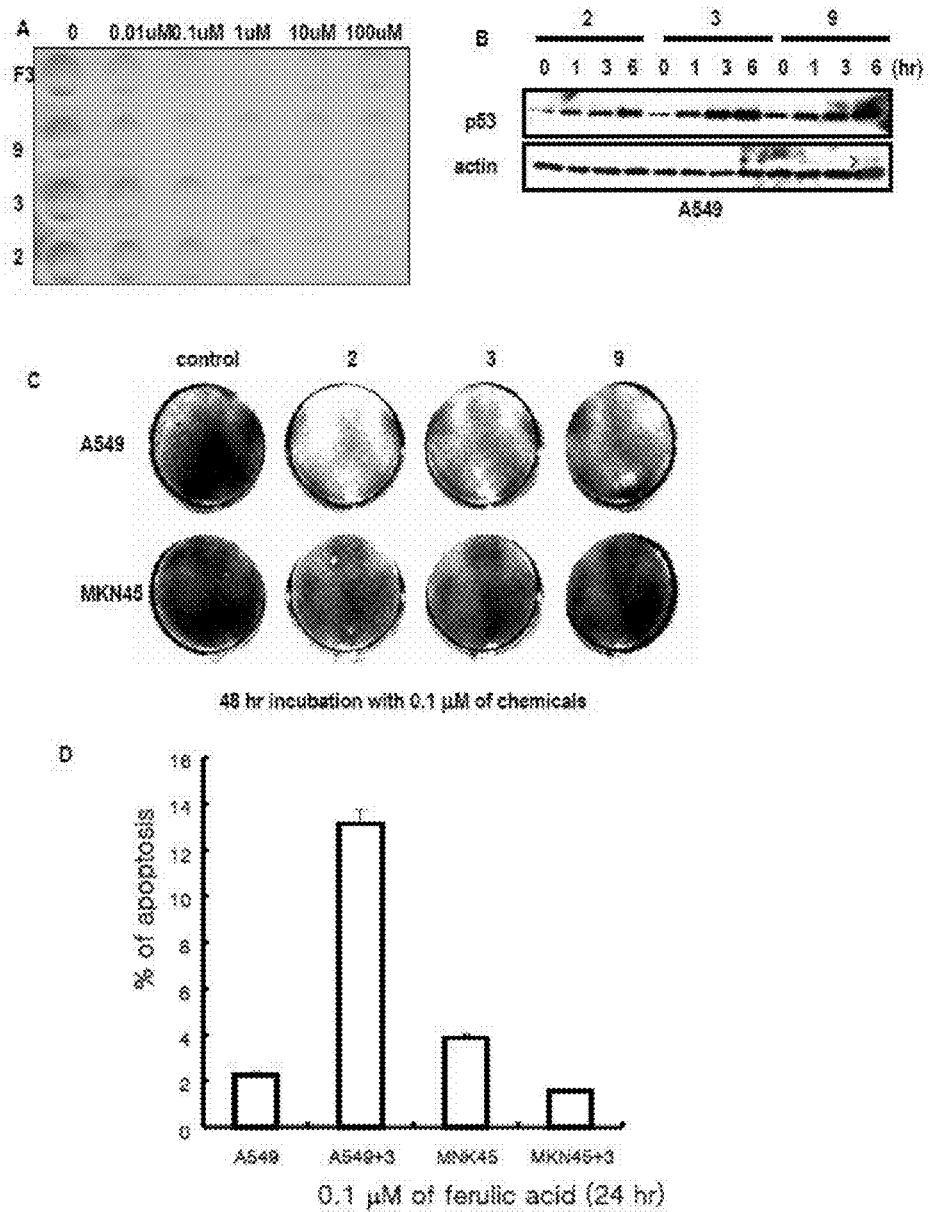

As shown in FIGS. 9A and 9B, p53 and SNAIL binding inhibition was checked by ELISA system. As shown in FIG. 9C, from about 150 chemicals, 3 kinds of chemicals were identified as an inhibitor of SNAIL and p53 binding. As shown in FIGS. 10A and 11A, these chemicals showed dose-dependent inhibition of SNAIL and p53 binding.

Through the GST-pull down assay, the expression of p53 and its targets after treatment of these chemicals was measured, and it was found that all of them blocked the interaction of p53 and SNAIL and induced p53 expression (see FIGS. 8B and 11B).

Also, as shown in FIG. 10C, induction of PUMA and p21 being treated with the chemicals was observed. In particular, induction of p53 was detected only in K-Ras mutated cells but not in wild type K-Ras harboring cells (see FIG. 10D). Similar structure of quercetin and morin suggested that the screening system of the present invention was reliable (see FIG. 10E).

Also, the effect of the chemicals on SNAIL-mediated p53 suppression was checked. As shown in FIGS. 10E and 10F, p53 reduction by co-transfection of SNAIL was blocked by treatment of chemicals by #3 and #9. These results suggested that blocking of p53-SNAIL interaction was restored the p53 expression.

Also, the effect of these chemicals on cell proliferation was examined using tryphan blue staining. It was found that these chemicals obviously suppressed cell proliferation in A549, whereas they did not show anti-proliferating effect on MKN45 (see FIG. 11C).

Also, ferulic acid evoked cell death in K-Ras mutated cells (see FIG. 11D). Moreover, Quercetin (#2) was identified as an inhibitor of SNAIL-p53 interaction.

K-Ras Mutant Cells Specific Drug Delivery Method Using Endocytosis of DNA Binding Domain of p53

Example 5

1. Exporting Mechanism of p53 from a Nucleus to a Cytoplasm

To perform a GST-pull down assay, first, a human SNAIL and p53 recombinant protein was prepared using a known method (Neoplasia 11: 1-10, 2009). To identify a direct binding between p53 and SNAIL in media and whole cell lysate, agarose bead conjugated GST or GST-SNAIL was incubated with cell lysate or culture media at 4° C. for 2 hours. After washing with PBS and RIPA, precipitated protein was subjected into SDS PAGE and WB by using the same method as described above.

2. Experimental Results

Figure 13:
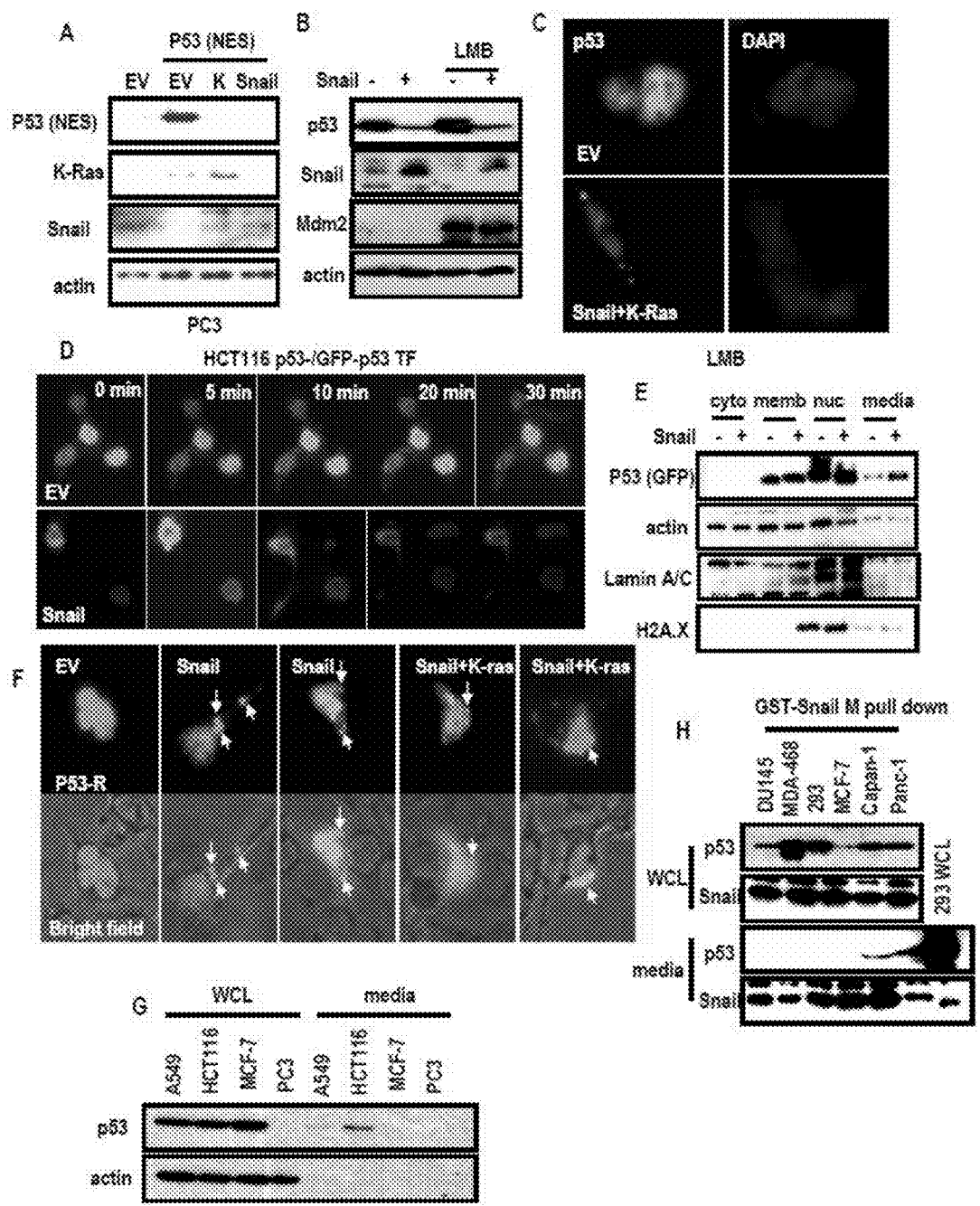
FIG. 13 shows results of an exporting mechanism of p53 from a nucleus to a cytoplasm.

The effect of SNAIL on p53 NES that is mutated in a p53 nuclear exporting sequence from a nucleus to a cytoplasm was checked, and it was found that SNAIL reduced p53 NES expression (see FIG. 13A) and leptomycin B(LMB; nuclear exporting blocker from a nucleus to a cytoplasm) did not block the SNAIL-mediated p53 reduction (see FIGS. 13B and 13C). The reduction of p53 by SNAIL was confirmed in real time (see FIG. 13D). Expression of p53 in culture-media was checked and within 2 hours, the expression of p53 in media was detected (see FIG. 13E). Moreover, p53 was detected in cytosol as a vesicle-like-structure in SNAIL or K-Ras transfected cells, and finally detected in an extracellular region (see FIG. 13F). Meanwhile, SNAIL was located in vesicle of cytosol with p53 (see FIG. 17A).

To confirm secretion of p53 in K-Ras mutated cells, the GST-Pull down assay was performed using SNAIL-GST in culture media and cell lysates. It was confirmed that although SNAIL-associated p53 was detected in all cell lysates, the median p53 was observed only in K-Ras mutated pancreatic cancer cell lines (see FIG. 13G). Also, the median p53 was identified in K-Ras mutated cell's culture media, without SNAIL-pull down (see FIG. 13H).

Figure 14:
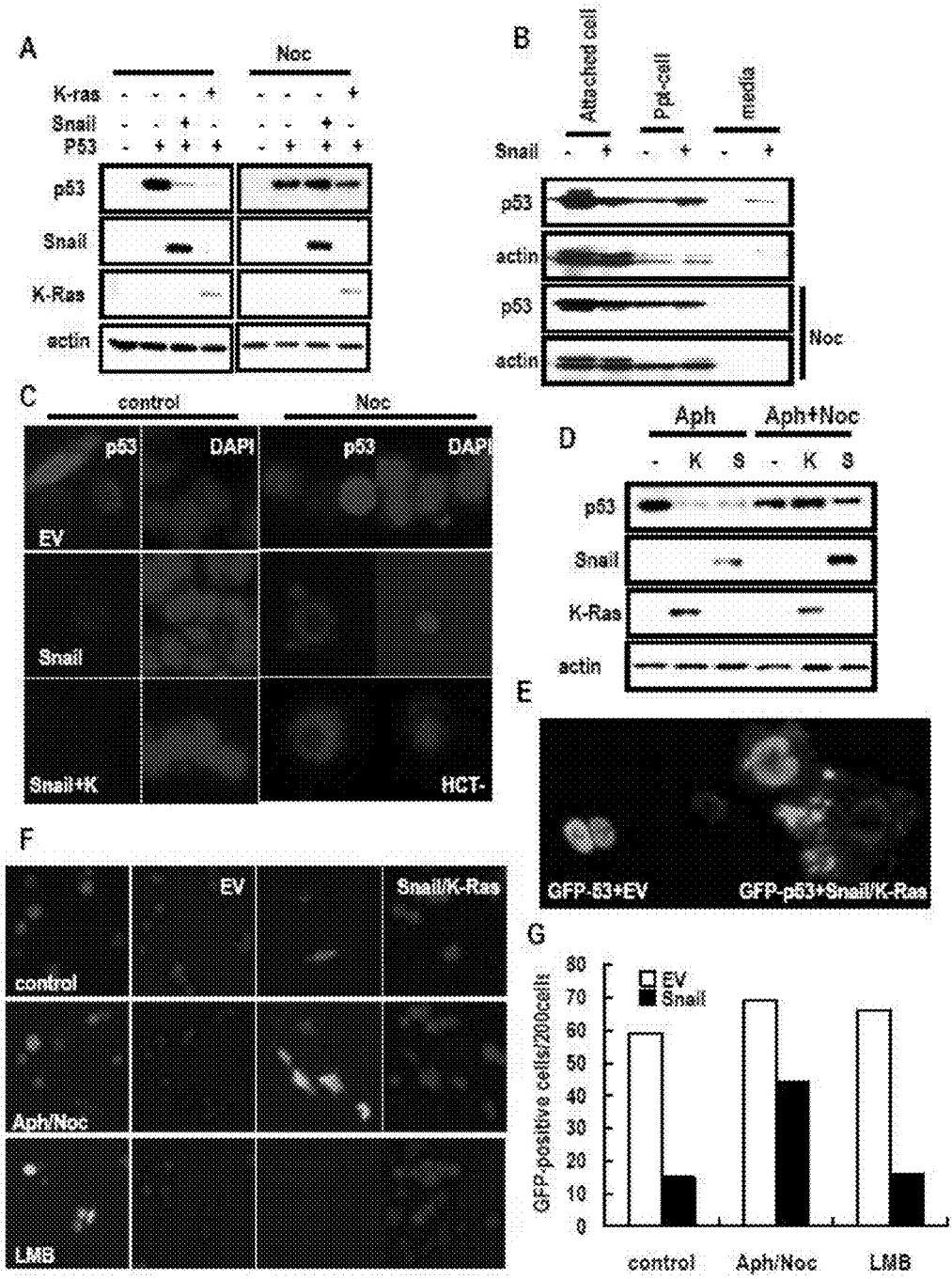
FIG. 14 shows that p53 is secreted through vesicle-transport.

Since p53 is reduced by vesicle-like transport, p53 expression was checked by disrupting cytoskeleton-network by Nocodazole (Noc). It was found that the Noc treatment blocked the SNAIL or K-Ras mediated p53 reduction (see FIG. 14A). Despite of cytoplasmic vesicle-like staining of p53 in Noc-treated cells, cellular morphology was changed differentially from control cells (see FIG. 14B). Noc blocked the p53 reduction (see FIG. 14C). Median p53 was disappeared by Noc-treatment, whereas p53 was accumulated in cytoplasm as vesicle (see FIGS. 14D and 14E). Aph/Noc blocked the reduction of p53, which was not achieved by LMB (FIGS. 14F and 14G).

Example 6

1. Behaviors of Extracellular p53 and SNAIL

1) Tissue Analysis

Normal and tumor paired cholangioma and liver tissues were obtained from Shunchunhyang Medical Center. Tissues were rapidly frozen in the deep freezer until use. Frozen tissues were sliced and 0.5 mg of tissues was incubated in 0.25 ml serum free medium for 30 min. at 37° C. to allow the release of tissue fluid. After incubation, the culture medium was collected and precipitated with 0.5 ml 100% Et-OH. Precipitated materials were dissolved using RIPA and used for SDS-PAGE and WB analysis. We also obtained same culture medium through the same method and used the culture medium to detect p53 antibody.

2) p53 ELISA Assay

To examine the p53, we performed the ELISA following manufacture's protocol (Assay Design). In brief, 0.2 ml tissue cultured media was added to wells and incubated with detection antibody. After washing with a wash buffer, 0.2 ml of a substrate sol and 0.05 ml of a stop solution were added thereto.

3) SNAIL Antibody Detection in Blood Samples

Human blood samples were obtained from Shunchunhyang University (pancreatic cancer and gall stone patients), and the medical center of Pusan National University (lung cancer). Normal blood samples were collected from volunteers or non-cancer patients. Serum was collected by centrifugation and kept at −70° C. until use. 3 µl of serum was incubated with agarose-conjugated GST-SNAIL-N after pre-clearing with GST-protein. Precipitated GST-SNAIL-antibody complex was dissolved with RIPA and SDS sample buffer, and subjected into SDS-PAGE in the same method as described above. After transfer to PVDF membrane, protein was incubated with anti-human antibody and anti-GST antibody.

2. Experimental Results

Figure 15:
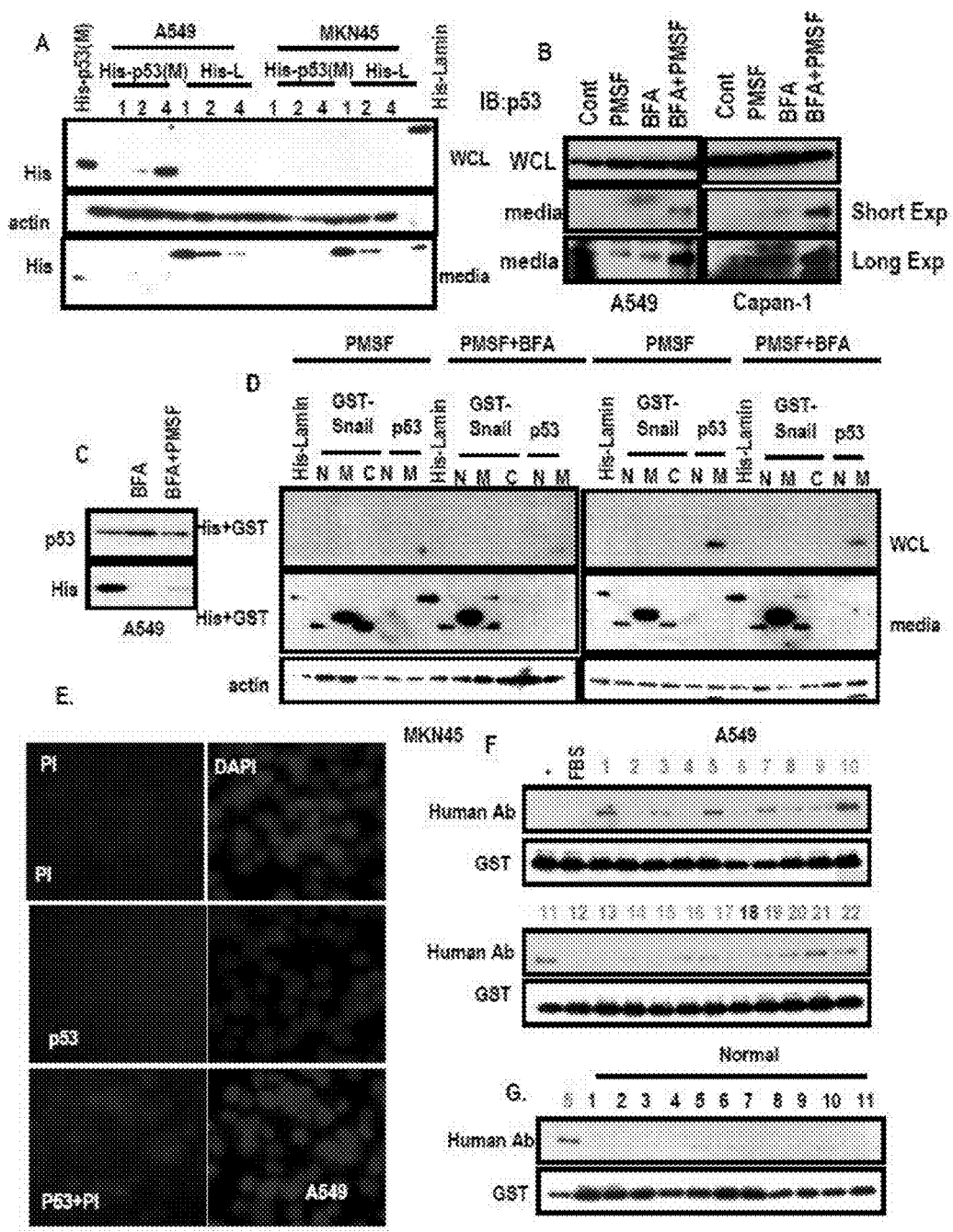
FIG. 15 shows results that p53 is removed by protease and endocytosis, and SNAIL shows a resistance to protease and endocytosis.

First, A549 and MKN 45 cells were treated with recombinant p53, and their locations were identified. In comparison with control protein (His-lamin A) recovered from media, His-p53 was expressed in whole cell lysate of A549 (FIG. 15A). In addition, His-p53 was completely removed from MKN45 cells and culture media thereof (FIG. 15A).

To get more detail, in the present invention, recombinant p53 was cultured using fresh media, A549-culture media, PC3, and HCT116. In comparison with His-laminA recovered from media, p53-His was detected in whole cell lysate of HCT116. In addition, p53 was not recovered neither from A549 culture media nor PC3. These results show that p53 was digested by protease that was secreted from cultured cells and also resorpted by K-Ras mutated cells.

Also, protease inhibitor (PMSF) and endocytosis inhibitor (Brefeldin A; BFA) were treated into A549 and Capan-1. Despite of non-effect on intrecellular p53 expression, both chemicals increased expression of median p53 (see FIG. 15B). BFA blocked the location of recombinant p53 in A549 whole cell lysate (FIG. 15C).

To know the behavior of secreted SNAIL, treatment with recombinant SNAIL was performed and the p53 destination was compared. p53 middle region was recovered from WCL of A549, which was suppressed by BFA. But recombinant p53, treated in MKN 45, was disappeared in media and in WCL. These results suggested that secreted p53 would be digested by not only serine protease but also other kinds of proteases such as MMP. Meanwhile, SNAIL was recovered from media, and the recombinant SNAIL was recovered without protease inhibitor. These results suggested that SNAIL would be resistant to endocytosis as well as protease-mediated digestion.

The effect of K-Ras on p53-endocytosis was measured and it was found that recombinant p53 was selectively eliminated by K-ras transfected cells. If p53 middle region could be re-entered by K-Ras mutated cells selectively, this property would be useful for chemical delivery to K-Ras mutated cells.

Figure 16:
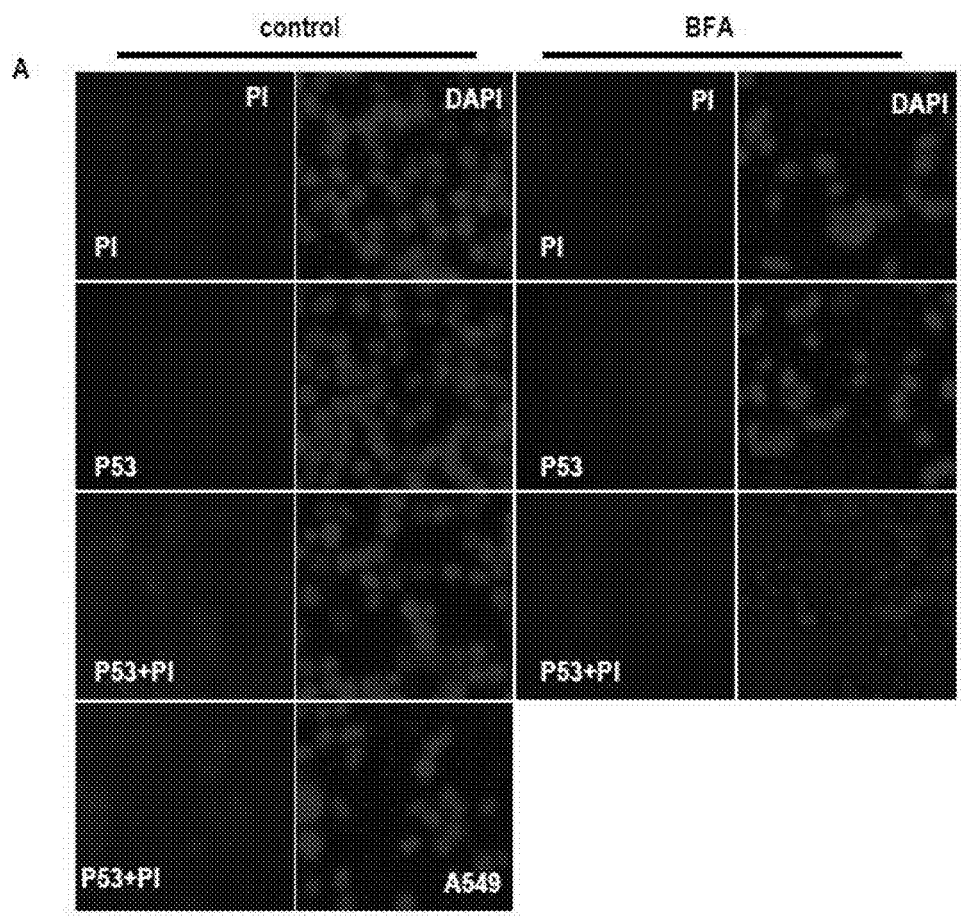
FIG. 16 shows re-absorption of His-p53 in K-Ras mutant cells.

To confirm this, PI (propidium iodine; red dye, 50 μg/mL) and His-p53 (2 μg/mL) were treated into A549 and MKN 45. PI alone was not accumulated into cells in both cell lines. When, however, PI and p53 were co-treated, PI, but not MKN 45, was accumulated in inner cells of A549 (FIGS. 15E, and 16A to 16B). These results suggested that p53 could be useful for K-Ras specific drug delivery system.

Figure 17:
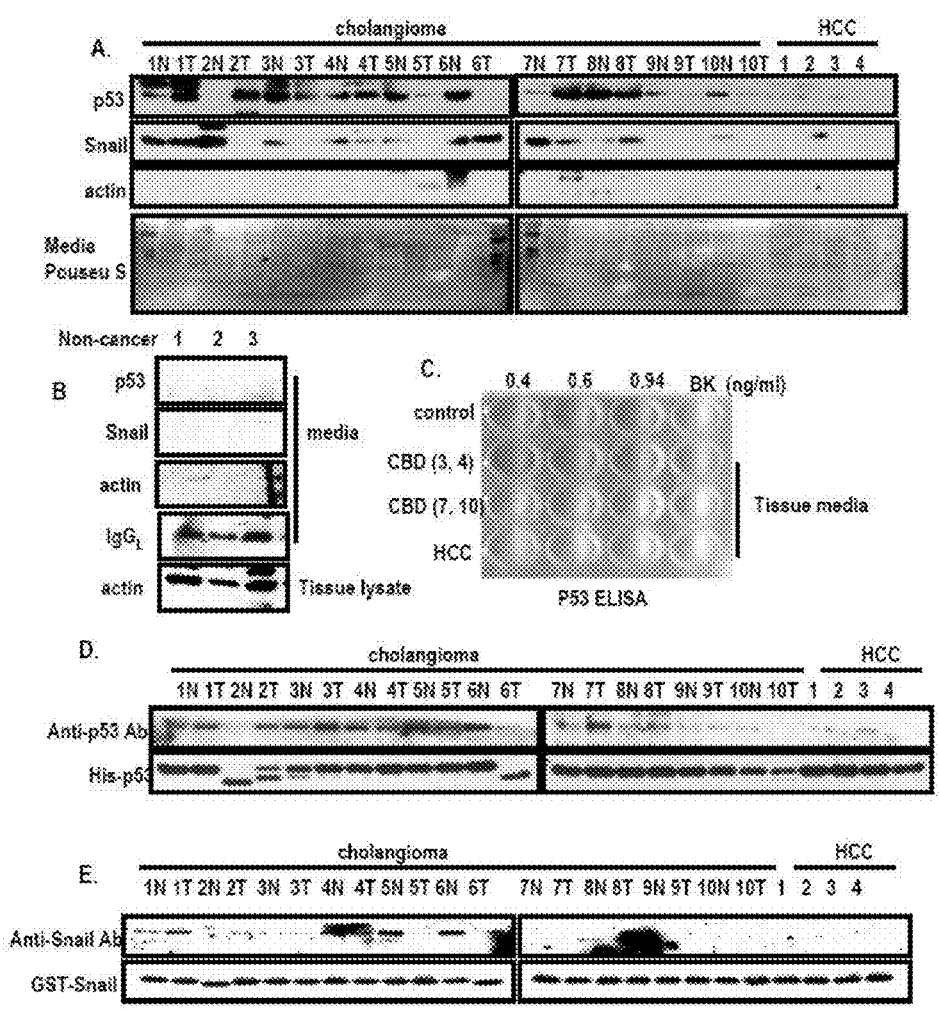
FIG. 17 shows secretion of p53 and SNAIL in cancer tissues.

To check whether autoantibody of p53 is produced by SNAIL-mediated secreted p53, p53 and SNAIL expression in tissue-fluid was identified. p53 and SNAIL were detected in cholangioma, but not in hepatocellular carcinoma (HCC) and non-cancer tissue fluid (see FIGS. 17A and 17B). As shown in FIG. 17C, the presence of p53 in tissue fluid was examined using ELISA. It was found that anti-p53 antibody and anti-SNAIL antibody were detected in cholangioma, but not in HCC (see FIGS. 17D and 17E). In addition, autoantibody against p53 and SNAIL in pancreatic or Bile duct cancer patient's blood serum was examined, and it was confirmed that anti-p53 antibody did not show relevance with cancer. These results suggested that p53 autoantibody did not show relevance with cancer status, and secreted p53 was rapidly removed by protease and endocytosis (see FIG. 15A).

Figure 18:
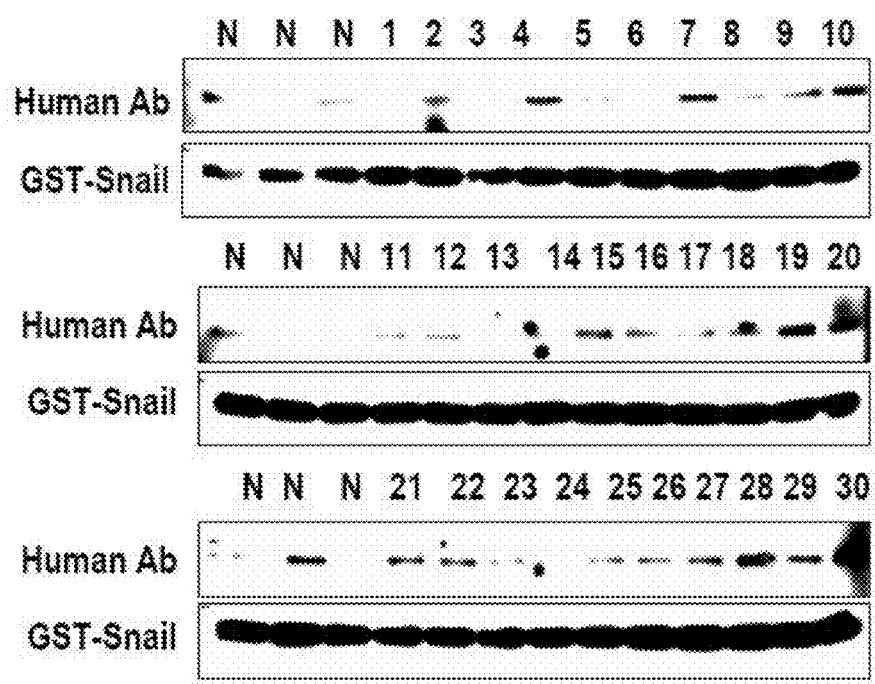
FIG. 18 shows analysis results of anti-SNAIL antibody in a lung cancer serum.
Figure 19:
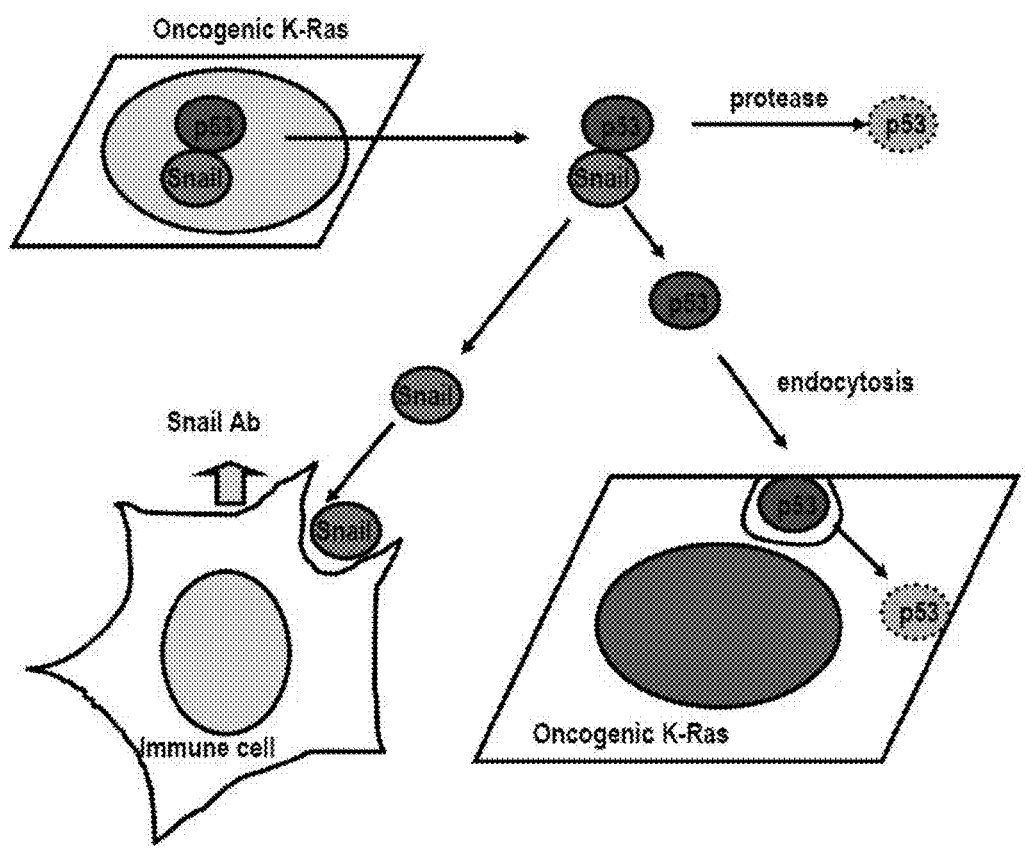
FIG. 19 shows schematic secretion morphology of p53 and SNAIL in oncogenic K-Ras.

In contrast, SNAIL was resistant to protease and endocytosis (FIG. 15D). Thus, SNAIL autoantibody in serum was checked. Expression of SNAIL antibody was detected in pancreatic cancer patient's serum and gallstone patient's serum (see FIG. 15F). In contrast, SNAIL antibody was not detected in normal healthy population (see FIG. 15G). SNAIL antibody was detected in lung cancer patient's serum (FIG. 18). Accordingly, it was deemed that presence of SNAIL antibody would be very useful as a cancer diagnostic marker.

TABLE 1

| sample NO | Age | Sex | Stage | Diagnosis | serum p53 | serum Snail | anti-p53 Ab | anti-Snail Ab |
|---|---|---|---|---|---|---|---|---|
| 1 | 45 | F | IV | CBD cancer/adenocarcinoma | Y | Y | Y | Y |
| 2 | 78 | F | III | CBD cancer/adenocarcinoma | Y | Y | Y | Y |
| 3 | 58 | M | IIB | adenocarcinoma (intrahepatic cholagiocarcinoma) | Y | Y | Y | Y |
| 4 | 74 | M | IIA | CBD cancer/adenocarcinoma | Y | Y | Y | Y |
| 5 | 62 | M | IIB | Gall Bladder adenocarcinoma | Y | Y | Y | Y |
| 6 | 38 | M | IIA | CBD cancer/adenocarcinoma | Y | Y | Y | Y |
| 7 | 56 | F | IIB | adenocarcinoma (intrahepatic cholagiocarcinoma) | Y | Y | Y | Y |
| 8 | 59 | M | IIA | CBD cancer/adenocarcinoma | Y | Y | Y | Y |
| 9 | 68 | M | IB | Amulla of Vater adenocarcinoma | Y (weak) | N | N | Y |
| 10 | 54 | F | IIB | CBD cancer/adenocarcinoma | Y | Y | N | N |
| HCC | | | | | | | | |
| 1 | 58 | M | II | HCC | N | N | N | N |
| 2 | 43 | M | I | HCC | N | N | N | Y (weak) |
| 3 | 66 | M | III | HCC | N | N | N | Y (weak) |
| 4 | 63 | F | I | HCC | N | N | N | N |

TABLE 2

| No | sex/age | cell type | TNM | Stage | Meta | | Snail Ab |
|---|---|---|---|---|---|---|---|
| 1 | M/64 | ADC | T2N0M0 | IB | x | | |
| 2 | M/65 | ADC | T4N3M1 | IV | brain | lost to f/u | positive |
| 3 | M/73 | SQC | T4N3M1 | IV | Lung | | |
| 4 | M/68 | SQC | T4N2Mx | IIIB | ? | | positive |

TABLE 2-continued

| No | sex/age | cell type | TNM | Stage | Meta | | Snail Ab |
|----|---------|-----------|--------|-----------|------------|------------|----------|
| 5  | M/63    | SQC       | T4N2Mx | IIIB      | ?          |            |          |
| 6  | M/50    | ADC       | T4N3M1 | IV        | brain, bone|            |          |
| 7  | M/72    | SQC       | T4N2M1 | IV        | brain      |            | positive |
| 8  | M/66    | SQC       | T4N3Mx | IIIB      | ?          |            |          |
| 9  | M/65    | SQC       | T2N2Mx | IIIA      | ?          | NA         | positive |
| 10 | M/56    | SQC       | T2N1Mx | IIB       | ?          | NA         | positive |
| 11 | M/72    | SQC       | T4N2M1 | IV        | bone       | lost to f/u|          |
| 12 | M/58    | SQC       | T2N3M0 | IIIB      | x          | expired    |          |
| 13 | M/72    | ADC       | T1N2M0 | IIIA      | x          |            |          |
| 14 | M/80    | ADC       | T4N3M1 | IV        | bone       |            |          |
| 15 | M/71    | SQC       | T3N2M1 | IV        | lung       | expired    | positive |
| 16 | F/74    | SCLC      | —      | extensive | lung       | expired    |          |
| 17 | M/62    | SQC       | T4N3M1 | IV        | lung       |            |          |
| 18 | M/48    | non-cancer|        |           |            |            |          |
| 19 | M/73    | SQC       | T2N1Mx | IIB       | ?          | NA         | positive |
| 20 | M/63    | SQC       | T4N3M0 | IIIB      | x          | expired    | positive |
| 21 | F/64    | ADC       | T4N3M1 | IV        | lung       | NA         | positive |
| 22 | M/69    | SQC       | T4N3Mx | IIIB      | ?          |            | positive |
| 23 | M/80    | SQC       | T4N1Mx | IIIB      | ?          |            |          |
| 24 | F/47    | ADC       | T4N2M1 | IV        | lung       | lost to f/u|          |
| 25 | M/61    | SQC       | T2N3M0 | IIIB      | x          | expired    | positive |
| 26 | M/63    | SQC       | T2N3Mx | IIIB      | ?          |            | positive |
| 27 | F/65    | SCLC      | —      | limited   | x          |            | positive |
| 28 | M/62    | SQC       | T3N3Mx | IIIB      | ?          | NA         | positive |
| 29 | M/67    | ADC       | T4N3Mx | IIIB      | ?          |            | positive |
| 30 | F/53    | ADC       | T1N0M0 | IA        | —          |            | positive |

SNAIL-p53 Binding Inhibitor Identification

Example 1

1-1. Synthesis of 2-methylthio-1,4-naphthoquinone (1a)

0.617 mM 1,4-naphtoquinone was dissolved in 30 ml of methanol in 100 ml one-neck round flask, and 1.54 mM sodium thiomethoxide was added thereto and stirred overnight. 50 ml of saturated sodium chloride solution was added to the reaction mixture, followed by extraction three times with 50 ml of chloroform, and an organic layer was dehydrated with an anhydrous sodium sulfate and filtered. The filtrate was concentrated under reduced pressure and the obtained residue was re-crystallized with methanol to produce 2-methylthio-1,4-naphthoquinone that was yellow crystal.

Yield: 14.0%, melting point: 185-186° C., $^1$H-NMR (CDCl$_3$, 400 MHz): δ 8.12-8.07 (m, 2H), 7.78-7.70 (m, 2H), 6.58 (s, 1H), 2.40 (s, 3H), m/z 205.1 (M+H)$^+$.

1-2. Synthesis of 2-ethylthio-1,4-naphthoquinone (1b)

2-ethylthio-1,4-naphthoquinone that was yellow crystal was prepared in the same manner as in Example 1-1, except that ethylmercaptan was used instead of sodium thiomethoxide. The yield and properties of the synthesized compound are as follows.

Yield: 40.7%, melting point: 135-136° C., $^1$H-NMR (CDCl$_3$, 400 MHz): δ 8.12-8.08 (m, 2H), 7.78-7.69 (m, 2H), 6.62 (s, 1H), 2.87 (q, J=7.2 Hz, 2H), 1.44 (t, J=7.2 Hz, 3H), m/z 219.1 (M+H)$^+$.

1-3. Synthesis of 2-propylthylthio-1,4-naphthoquinone (1c)

2-propylthylthio-1,4-naphthoquinone that was yellow crystal was prepared in the same manner as in Example 1-1, except that propylmercaptan was used instead of sodium thiomethoxide. The yield and properties of the synthesized compound are as follows.

Yield: 33.9%, melting point: 118-119° C., $^1$H-NMR (CDCl$_3$, 400 MHz): δ 8.12-8.07 (m, 2H), 7.77-7.68 (m, 2H), 6.61 (s, 1H), 2.82 (t, J=7.6 Hz, 2H), 1.86-1.77 (m, 2H), 1.11 (t, J=7.2 Hz, 3H), m/z 233.0 (M+H)$^+$.

1-4. Synthesis of 2-butylthio-1,4-naphthoquinone (1d)

2-butylthio-1,4-naphthoquinone (1d) that was yellow crystal was prepared in the same manner as in Example 1-1, except that butylmercaptan was used instead of sodium thiomethoxide. The yield and properties of the synthesized compound are as follows.

Yield: 33.9%, melting point: 97-98° C., $^1$H-NMR (CDCl$_3$, 400 MHz): δ 8.12-8.07 (m, 2H), 7.77-7.68 (m, 2H), 6.61 (s, 1H), 2.84 (t, J=7.2 Hz, 2H), 1.80-1.72 (m, 2H), 1.57-1.48 (m, 2H), 0.98 (t, J=7.6 Hz, 3H), m/z 247.1 (M+H)$^+$.

1-5. Synthesis of 2-pentylthio-1,4-naphthoquinone (1e)

2-pentylthio-1,4-naphthoquinone that was yellow crystal was prepared in the same manner as in Example 1-1, except that pentylmercaptan was used instead of sodium thiomethoxide. The yield and properties of the synthesized compound are as follows.

Yield: 15.3%, melting point: 111-112° C., $^1$H-NMR (CDCl$_3$, 400 MHz): δ 8.11-8.06 (m, 2H), 7.77-7.68 (m, 2H), 6.60 (s, 1H), 2.83 (t, J=7.6 Hz, 2H), 2.17-1.74 (m, 2H), 1.51-1.33 (m, 4H), 0.93 (t, J=7.2 Hz, 3H), m/z 261.2 (M+H)$^+$.

1-6. Synthesis of 2-hexylthio-1,4-naphthoquinone (1e)

2-hexylthio-1,4-naphthoquinone that was yellow crystal was prepared in the same manner as in Example 1-1, except that hexylmercaptan was used instead of sodium thiomethoxide. The yield and properties of the synthesized compound are as follows.

Yield: 15.0%, melting point: 101-102° C., $^1$H-NMR (CDCl$_3$, 400 MHz): δ 8.13-8.08 (m, 2H), 7.77-7.69 (m, 2H), 6.61 (s, 1H), 2.83 (t, J=7.6 Hz, 2H), 1.81-1.73 (m, 2H), 1.56-1.46 (m, 2H), 1.35-1.31 (m, 4H), 0.91 (t, J=6.8 Hz, 3H), m/z 275.3 (M+H)$^+$.

1-7. Synthesis of 2-heptylthio-1,4-naphthoquinone (1g)

2-heptylthio-1,4-naphthoquinone that was yellow crystal was prepared in the same manner as in Example 1-1, except that heptylmercaptan was used instead of sodium thiomethoxide. The yield and properties of the synthesized compound are as follows.

Yield: 46.4%, melting point: 114-115° C., $^1$H-NMR (CDCl$_3$, 400 MHz): δ 8.12-8.07 (m, 2H), 7.77-7.68 (m, 2H), 6.61 (s, 1H), 2.83 (t, J=14.8 Hz, 2H), 1.77 (quint, J=7.6 Hz, 2H), 1.52-1.45 (m, 2H), 1.35-1.29 (m, 6H), 0.90 (t, J=6.8 Hz, 3H), m/z 289.2 (M+H)$^+$.

1-8. Synthesis of 2-octylthio-1,4-naphthoquinone (1h)

2-octylthio-1,4-naphthoquinone that was yellow crystal was prepared in the same manner as in Example 1-1, except that octylmercaptan was used instead of sodium thiomethoxide. The yield and properties of the synthesized compound are as follows.

Yield: 76.8%, melting point: 114-115° C., $^1$H-NMR (CDCl$_3$, 400 MHz): δ 8.12-8.10 (m, 2H), 7.78-7.70 (m, 2H), 6.61 (s, 1H), 2.84 (t, J=7.6 Hz, 2H), 1.77 (quint, J=7.6 Hz, 2H), 1.49-1.47 (m, 2H), 1.35-1.29 (m, 8H), 0.89 (t, J=6.8 Hz, 3H), m/z 304.5 (M+H)$^+$.

1-9. Synthesis of 2-nonylthio-1,4-naphthoquinone (1i)

2-nonylthio-1,4-naphthoquinone that was yellow crystal was prepared in the same manner as in Example 1-1, except that nonylmercaptan was used instead of sodium thiomethoxide. The yield and properties of the synthesized compound are as follows.

Yield: 87.4%, melting point: 105-106° C., $^1$H-NMR (CDCl$_3$, 400 MHz): δ 8.12-8.07 (m, 2H), 7.77-7.68 (m, 2H), 6.61 (s, 1H), 2.83 (t, J=7.6 Hz, 2H), 1.77 (quint, J=7.6 Hz, 2H), 1.51-1.45 (m, 2H), 1.33-1.29 (m, 10H), 0.89 (t, J=6.4 Hz, 3H), m/z 317.5 (M+H)$^+$.

1-10. Synthesis of 2-decylthio-1,4-naphthoquinone (1-j)

2-decylthio-1,4-naphthoquinone that was yellow crystal was prepared in the same manner as in Example 1-1, except that decylmercaptan was used instead of sodium thiomethoxide. The yield and properties of the synthesized compound are as follows.

Yield: 87.4%, melting point: 101-102° C., $^1$H-NMR (CDCl$_3$, 400 MHz): δ 8.12-8.08 (m, 2H), 7.77-7.68 (m, 2H), 6.61 (s, 1H), 2.83 (t, J=7.2 Hz, 2H), 1.77 (quint, J=7.6 Hz, 2H), 1.50-1.42 (m, 2H), 1.33-1.29 (m, 12H), 0.88 (t, J=6.4 Hz, 3H), m/z 331.1 (M+H)$^+$.

Example 2

2-1. Synthesis of 2-methylamino-5,8-dimethoxy-1,4-naphthoquinone (5a)

0.45 mM 5,8-dimethoxy-1,4-naphthoquinone (4) which had been prepared above was dissolved in 30 ml of methanol in 100 ml one-neck round flask and then, 0.687 mmol methylamine was added thereto and stirred at room temperature for 3 hours 0.64 mM sodium dichromate and 0.18 mM sulfuric acid dissolved in water were slowly dropped to the reaction mixture and stirred at room temperature for 3 minutes. Then, 50 ml of saturated sodium chloride was added to the reaction mixture, followed by extraction three times with 50 ml of chloroform and obtained organic layers were gathered and dehydrated with anhydrous sodium sulfate and filtered. The filtrate was concentrated under reduced pressure and the residue was subjected to silicagel column chromatography, thereby producing 2-methylamino-5,8-dimethoxy-1,4-naphthoquinone that was reddish brown. The yield and properties of the synthesized compound are as follows.

Yield: 56.7%, melting point: 203-204° C., $^1$H-NMR (CDCl$_3$, 400 MHz): δ 7.34 (d, J=9.6 MHz), 7.19 (d, J=9.2 MHz, 1H), 5.75 (BR, 1H), 5.60 (s, 1H), 3.96 (s, 3H), 3.94 (s, 3H), 2.87 (d, J=5.2 MHz, 3H), m/z 248 (M+H)$^+$.

2-2. Synthesis of 2-ethylamino-5,8-dimethoxy-1,4-naphthoquinone (5b)

2-ethylamino-5,8-dimethoxy-1,4-naphthoquinone (5b) was prepared in the same manner as in Example 2-1, except that ethylamine was used instead of methylamine in the round flask of Example 2-1. The yield and properties of the synthesized compound are as follows.

Yield: 23.6%, melting point: 172-173° C., $^1$H-NMR (CDCl$_3$, 400 MHz): δ 7.34 (d, J=9.2 Hz, 1H), 7.19 (d, J=9.6 Hz, 1H), 5.63 (BR, 1H), 5.61 (s, 1H), 3.96 (s, 3H), 3.94 (s, 3H), 3.09 (q, 2H), 1.29 (t, J=7.2 Hz, 3H), m/z 262.1 (M+H)$^+$.

2-3. Synthesis of 2-propylamino-5,8-dimethoxy-1,4-naphthoquinone (5c)

2-propylamino-5,8-dimethoxy-1,4-naphthoquinone (5c) was prepared in the same manner as in Example 2-1, except that propylamine was used instead of methylamine in the round flask of Example 2-1. The yield and properties of the synthesized compound are as follows.

Yield: 46.5%, melting point: 175-176° C., $^1$H-NMR (CDCl$_3$, 400 MHz): δ 7.34 (d, J=9.2 Hz, 1H), 7.19 (d, J=9.2 Hz, 1H), 5.72 (BR, 1H), 5.61 (s, 1H), 3.96 (s, 3H), 3.94 (s, 3H), 3.09 (q, 2H), 1.68 (J=6.8 Hz, 2H), 0.99 (t, J=7.6 Hz, 3H), m/z 276 (M+H)$^+$.

2-4. Synthesis of 2-butylamino-5,8-dimethoxy-1,4-naphthoquinone (5d)

2-butylamino-5,8-dimethoxy-1,4-naphthoquinone (5d) was prepared in the same manner as in Example 2-1, except that butylamine was used instead of methylamine in the round flask of Example 2-1. The yield and properties of the synthesized compound are as follows.

Yield: 46.2%, melting point: 104-105° C., $^1$H-NMR (CDCl$_3$, 400 MHz): δ 7.34 (d, J=9.6 Hz, 1H), 7.19 (d, J=9.6

Hz, 1H), 5.70 (BR, 1H), 5.61 (s, 1H), 3.96 (s, 3H), 3.94 (s, 3H), 3.11 (q, 2H), 1.64 (p, 2H), 1.46-1.38 (m, 2H), 0.95 (t, J=7.2 Hz, 3H), m/z 290 (M+H)$^+$.

2-5. Synthesis of 2-pentylamino-5,8-dimethoxy-1,4-naphthoquinone (5e)

2-pentylamino-5,8-dimethoxy-1,4-naphthoquinone (5e) was prepared in the same manner as in Example 2-1, except that pentylamine was used instead of methylamine in the round flask of Example 2-1. The yield and properties of the synthesized compound are as follows.

Yield: 55.9%, melting point: 102-103° C. $^1$H-NMR (CDCl$_3$, 400): δ 7.34 (d, j=9.2 MHz, 1H), 7.19 (d, J=9.2 Hz, 1H), 5.70 (BR, 1H), 5.61 (s, 1H), 3.96 (s, 3H), 3.94 (s, 3H), 3.11 (q, 2H), 1.29 (t, J=7.2 Hz, 3H), m/z 303.6 (M+H)$^+$.

2-6. Synthesis of 2-hexylamino-5,8-dimethoxy-1,4-naphthoquinone (5f)

2-hexylamino-5,8-dimethoxy-1,4-naphthoquinone (5f) was prepared in the same manner as in Example 2-1, except that hexylamine was used instead of methylamine in the round flask of Example 2-1. The yield and properties of the synthesized compound are as follows.

Yield: 47.3%, melting point: 83-84° C., $^1$H-NMR (CDCl$_3$, 400 MHz): δ 7.34 (d, J=9.6 Hz, 1H), 7.18 (d, J=9.6 Hz, 1H), 5.69 (BR, 1H), 5.61 (s, 1H), 3.96 (s, 3H), 3.94 (s, 3H), 3.11 (q, 2H), 1.66-1.58 (m, 4H), 1.32-1.30 (m, 4H), 0.89 (t, J=6.8 Hz, 3H), m/z 318 (M+H)$^+$.

2.7 Synthesis of 2-heptylamino-5,8-dimethoxy-1,4-naphthoquinone (5g)

2-heptylamino-5,8-dimethoxy-1,4-naphthoquinone (5g) was prepared in the same manner as in Example 2-1, except that heptylamine was used instead of methylamine in the round flask of Example 2-1. The yield and properties of the synthesized compound are as follows.

Yield: 41.8%, melting point: 74-75° C., $^1$H-NMR (CDCl$_3$, 400 MHz): δ 7.34 (d, J=9.6 Hz, 1H), 7.33 (d, j=9.6 Hz, 1H), 7.18 (d, J=9.6 Hz, 1H), 5.69 (BR, 1H), 5.60 (s, 1H), 3.96 (s, 3H), 3.94 (s, 3H), 3.11 (q, 2H), 1.66-1.61 (m, 2H), 1.35-1.29 (m, 8H), 0.89 (t, J=6.4 Hz, 3H), m/z 332 (M+H)$^+$.

2-8. Synthesis of 2-octylamino-5,8-dimethoxy-1,4-naphthoquinone (5h)

2-octylamino-5,8-dimethoxy-1,4-naphthoquinone (5h) was prepared in the same manner as in Example 2-1, except that octylamine was used instead of methylamine in the round flask of Example 2-1. The yield and properties of the synthesized compound are as follows.

Yield: 45.1%, melting point: 81-82° C., $^1$H-NMR (CDCl$_3$, 400 MHz): δ 7.34 (d, j=9.6 Hz, 1H), 7.18 (d, J=9.6 Hz, 1H), 5.69 (br, 1H), 5.61 (s, 1H), 3.96 (s, 3H), 3.94 (s, 3H), 3.11 (q, 2H), 1.68-1.61 (m, 2H), 1.41-1.20 (m, 10H), 0.88 (t, J=6.4 Hz, 3H), m/z 346 (M+H)$^+$.

2-9. Synthesis of 2-nonylamino-5,8-dimethoxy-1,4-naphthoquinone (5i) 2-nonylamino-5,8-dimethoxy-1,4-naphthoquinone (5i) was prepared in the same manner as in Example 2-1, except that nonylamine was used instead of methylamine in the round flask of Example 2-1. The yield and properties of the synthesized compound are as follows.

Yield: 44.0%, melting point: 85-86° C., $^1$H-NMR (CDCl$_3$, 400 MHz): δ 7.34 (d, j=9.6 Hz, 1H), 7.18 (d, J=9.6 Hz, 1H), 5.69 (br, 1H), 5.61 (s, 1H), 3.96 (s, 3H), 3.94 (s, 3H), 3.11 (m, 2H), 1.66-1.61 (m, 2H), 1.41-1.20 (m, 12H), 0.88 (t, J=6.4 Hz, 3H), m/z 360 (M+H)$^+$.

2-10. Synthesis of 2-decylamino-5,8-dimethoxy-1,4-naphthoquinone (5j)

2-decylamino-5,8-dimethoxy-1,4-naphthoquinone (5j) was prepared in the same manner as in Example 2-1, except that decylamine was used instead of methylamine in the round flask of Example 2-1. The yield and properties of the synthesized compound are as follows.

Yield: 17.6%, melting point: 86-87° C., $^1$H-NMR (CDCl$_3$, 400 MHz): δ7.33 (d, j=9.2 Hz, 1H), 7.18 (d, J=9.2 Hz, 1H), 5.69 (br, 1H), 5.60 (s, 1H), 3.96 (s, 3H), 3.94 (s, 3H), 3.11 (q, 2H), 1.66-1.61 (m, 2H), 1.40-1.20 (m, 14H), 0.88 (t, J=6.4 Hz, 3H), m/z 374 (M+H)$^+$.

2-11. Synthesis of 2-(2-hydroxyethylthio)-5,8-dimethoxy-1,4-naphthoquinone (5k)

2-(2-Hydroxyethylthio)-5,8-dimethoxy-1,4-naphthoquinone (5k) was prepared in the same manner as in Example 2-1, except that 2-mercaptoethanol was used instead of methylamine in the round flask of Example 2-1. The yield and properties of the synthesized compound are as follows.

Yield: 59.5% melting point: 117-118° C., $^1$H-NMR (CDCl$_3$, 400 MHz): δ7.34 (d, J=9.6 Hz, 1H), 7.28 (d, J=9.6 Hz, 1H), 6.61 (s, 1H), 3.96 (s, 6H), 3.93 (t, J=6.4 Hz, 2H), 3.05 (t, J=6.4 Hz, 2H), m/z 316.9 (M+Na)$^+$.

2-12. Synthesis of 2-(3-hydroxypropylthio)-5,8-dimethoxy-1,4-naphthoquinone (5l)

2-(3-Hydroxypropylthio)-5,8-dimethoxy-1,4-naphthoquinone (5l) was prepared in the same manner as in Example 2-1, except that 3-mercaptopropanol was used instead of methylamine in the round flask of Example 2-1. The yield and properties of the synthesized compound are as follows.

Yield: 69.9%, melting point: 125~126° C., $^1$H-NMR (CDCl$_3$, 400 MHz): δ7.33 (d, J=9.6 Hz, 1H), 7.27 (d, J=9.6 Hz, 1H), 6.51 (s, 1H), 3.96 (s, 6H), 3.81 (t, J=6.4 Hz, 2H), 2.91 (t, J=7.2 Hz, 2H), 1.99 (m, 2H), m/z 331.1 (M+Na)$^+$.

2-13. Synthesis of 2-(4-hydroxybutylthio)-5,8-dimethoxy-1,4-naphthoquinone (5m)

2-(4-Hydroxybutylthio)-5,8-dimethoxy-1,4-naphthoquinone (5m) was prepared in the same manner as in Example 2-1, except that 4-mercaptobutanol was used instead of methylamine in the round flask of Example 2-1. The yield and properties of the synthesized compound are as follows.

Yield: 64.0%, melting point: 122-123° C., $^1$H-NMR (CDCl$_3$, 400 MHz): δ 7.33 (d, J=9.6 Hz, 1H), 7.29 (d, J=10.0 Hz, 1H), 6.46 (s, 1H), 3.96 (s, 3H), 3.95 (s, 3H), 3.71 (t, J=6.4 Hz, 2H), 1.87-1.81 (m, 2H), 1.78-1.50 (m, 2H), m/z 345.1 (M+Na)$^+$.

2-14. Synthesis of 2-(6-hydroxyhexylthio)-5,8-dimethoxy-1,4-naphthoquinone (5n)

2-(6-hydroxyhexylthio)-5,8-dimethoxy-1,4-naphthoquinone (5n) was prepared in the same manner as in Example 2-1, except that 6-mercaptohexanol was used instead of methylamine in the round flask of Example 2-1. The yield and properties of the synthesized compound are as follows.

Yield: 38.2% Melting point: 87~88° C., $^1$H-NMR (CDCl$_3$, 400 MHz): δ 7.33 (d, J=9.6 Hz, 1H), 7.27 (d, J=9.6 Hz, 1H), 6.45 (s, 1H), 3.96 (s, 6H), 3.66 (t, J=6.4 Hz, 2H), 2.76 (t, J=7.6 Hz, 2H), 1.78-1.12 (m, 2H), 1.61-1.25 (m, 6H), m/z 372.9 (M+Na)$^+$.

2-15. Synthesis of 3-(5,8-dimethoxy-1,4-dioxo-naphthalen-2-ylthio)propanoic acid (5o)

3-(5,8-dimethoxy-1,4-dioxo-naphthalen-2-ylthio)propanoic acid (5o) was prepared in the same manner as in Example 2-1, except that 3-mercaptopropionic acid was used instead of methylamine in the round flask of Example 2-1. The yield and properties of the synthesized compound are as follows.

Yield: 80.6%, melting point: 208~209° C., $^1$H-NMR (CDCl$_3$, 400 MHz): δ 7.35 (d, J=9.2 Hz, 1H), 7.28 (d, J=13.6 Hz, 1H), 6.51 (s, 1H), 3.97 (s, 3H), 3.96 (s, 3H), 3.07 (t, J=7.2 Hz, 2H), 2.81 (t, J=7.2 Hz, 2H), m/z 348.4 (M+Na)$^+$.

2-16. Synthesis of 11-(5,8-dimethoxy-1,4-dioxo-naphthalen-2-ylthio)undecanoic acid (5p)

11-(5,8-dimethoxy-1,4-dioxo-naphthalen-2-ylthio)undecanoic acid (5p) was prepared in the same manner as in Example 2-1, except that 11-mercaptoundecanoic acid was used instead of methylamine in the round flask of Example 2-1. The yield and properties of the synthesized compound are as follows.

Yield: 77.9%, melting point: 146-147° C., $^1$H-NMR (CDCl$_3$, 400 MHz): δ 7.33 (d, J=9.6 Hz, 1H), 7.27 (d, J=9.6 Hz, 1H), 6.46 (s, 1H), 3.96 (s, 3H), 3.95 (s, 3H), 3.34 (t, J=7.2 Hz, 2H), 2.75 (t, J=2.7 Hz, 2H), 2.41-2.32 (m, 5H), 2.06-2.00 (m, 2H), 1.76-1.56 (m, 5H), 1.48-1.39 (m, 2H), 0.97-0.88 (m, 2H), m/z 435 (M+H)$^+$

Example 3

3-1. Synthesis of 5, 8-dimethoxy-2-(3-oxo-3-(4-phenylpiperazin-1-yl)propylthio)naphthalene-1,4-dione (6a)

0.163 mM 3-(5,8-dimethoxy-1,4-dioxo-1,4-dihydronaphthalene-2-ylthio)propanoic acid that had been prepared above was dissolved in 40 ml of chloroform in 100 ml one-neck round flask, and then 0.26 mM N-(3-dimethylaminopropyl)-N'-ethylcarbodimide hydro chloride (EDC) and 0.26 mM 4-phenylpiperidine were added thereto and stirred overnight. 1N hydrochloric acid was added to the reaction mixture and stirred at room temperature for 3 minutes. Then, 50 ml of saturated sodium chloride solution was added thereto, followed by extraction three times with 50 ml of chloroform, and obtained organic layers were gathered and dehydrated with anhydrous sodium sulfate and filtered. The filtrate was concentrated under reduced pressure and the residue was subjected to silicagel column chromatography, thereby producing 5,8-dimethoxy-2-(3-oxo-3-(4-phenylpiperazin-1-yl)propylthio)naphthalene-1,4-dione (6a) that was reddish brown. The yield and properties of the synthesized compound are as follows.

Yield: 73.5%, melting point: 9495° C., H-NMR (CDCl$_3$, 400 MHz): δ7.34-7.28 (m, 5H), 7.19 (d, J=7.6 Hz), 6.26 (s, 1H), 3.95 (s, 3H), 3.94 (s, 3H), 314 (t, 4H), 2.79-2.74 (q, 4H), 2.67 (t, J=12 Hz, 1H), 1.89 (t, J=12.4 Hz, 2H), 1.65 (t, J=12.4 Hz, 2H), m/z 466.3 (M+H)$^+$.

Example 4

4-1. Synthesis of isobutyl-11-(5, 8-dimethoxy-1,4-dioxo-1,4-dihydronaphthalene-2-ylthio)undecanoate (7a)

1.15 mM 11-(5,8-dimethoxy-1,4-dioxo-1,4-dihydronaphthalene-2-ylthio)undecanoic acid (5p) that had been prepared above was dissolved in 60 ml of chloroform in 100 ml one-neck round flask and then, 1.38 mM N-(3-dimethylaminopropyl)-N'-ethylcarbodimide hydro chloride (EDC) and 1.38 mM isobutylalcohol were added thereto and stirred overnight. 1N hydrochloric acid was added to the reaction mixture and stirred at room temperature for 3 minutes. Then, 50 ml of saturated sodium chloride solution was added thereto, followed by extraction three times with 50 ml of chloroform, and obtained organic layers were gathered and dehydrated with anhydrous sodium sulfate and filtered. The filtrate was concentrated under reduced pressure and the residue was subjected to silicagel column chromatography, thereby producing isobutyl-11-(5,8-dimethoxy-1,4-dioxo-1,4-dihydronaphthalene-2-ylthio)undecanoate (7a) that was reddish brown. The yield and properties of the synthesized compound are as follows.

Yield: 52.4%, melting point: 58-59° C., $^1$H-NMR (CDCl$_3$, 400 MHz): δ 7.32 (d, J=9.6 Hz, 1H), 7.26 (d, J=9.6 Hz, 1H), 6.44 (s, 1H), 3.96 (s, 3H), 3.95 (s, 3H), 3.85 (d, J=6.8 Hz, 2H), 2.75 (t, J=7.6 Hz, 2H), 2.31 (t, 7.6 Hz, 2H), 1.96-1.89 (m, 1H), 1.72-1.68 (m, 4H), 1.29-1.25 (m, 12H), 0.94 (s, 3H), 0.92 (s, 3H), m/z 491 (M+H)$^+$

4-2. Synthesis of 11-(5,8-dimethoxy-1,4-dioxo-1,4-dihydronaphthalene-2-ylthio)-N-isobutyl undecanamide (7b)

11-(5,8-dimethoxy-1,4-dioxo-1,4-dihydronaphthalene-2-ylthio)-N-isobutyl undecanamide (7b) was prepared in the same manner as in Example 4-1, except that isobutylamine was used instead of isobutylalcohol in the round flask of Example 4-1. The yield and properties of the synthesized compound are as follows.

Yield: 77.9%, melting point: 74-75° C., $^1$H-NMR (CDCl$_3$, 400 MHz): δ 7.33 (d, J=9.6 Hz, 1H), 7.27 (d, J=9.2 Hz), 6.44 (s, 1H), 5.55 (s, 1H), 3.96 (s, 3H), 3.95 (s, 3H), 3.10 (t, J=6.6 Hz, 2H), 2.75 (t, J=7.6 Hz, 2H), 2.17 (t, J=7.4 Hz, 2H), 1.78-1.7 (m, 2H), 1.63 (m, 2H), 1.45 (m, 1H), 0.92 (s, 3H), 0.90 (s, 3H), m/z 490.0 (M+H)$^+$.

Example 5

5-1. Synthesis of isobutyl 11-(5,8-dimethoxyl-1,4-dioxo-1,4-dihydronaphthalene-2-yl sulfinyl) undecanoate (8)

0.163 mM isobutyl 11-(5,8-dimethoxy-1,4-dioxo-1,4-dihydroxynaphthalene-2-ylthio)-undecanoate (7a) that had been prepared above was dissolved in 30 ml of dichloromethane in 100 ml one-neck round flask and then 0.196 mM 3-chloroperoxybbenzoic acid was added thereto and stirred for 2 hours A sodium bicarbonate was added to the reaction mixture and stirred at room temperature for 3 minutes. Then, 50 ml of saturated sodium chloride solution was added thereto, followed by extraction three times with 50 ml of chloroform, and obtained organic layers were gathered and dehydrated with anhydrous sodium sulfate and filtered. The filtrate was concentrated under reduced pressure and the residue was subjected to silicagel column chromatography, thereby producing isobutyl 11-(5, 8-dimethoxyl-1,4-dioxo-1, 4-dihydronaphthalene-2-yl sulfinyl) undecanoate (8) that was red. The yield and properties of the synthesized compound are as follows.

Yield: 45.8%, melting point: 92~93° C., $^1$H-NMR (CDCl$_3$, 400 MHz): δ7.41 (d, J=9.6 Hz, 1H), 7.36 (d, J=9.6 Hz, 1H), 7.31 (s, 1H), 3.99 (s, 3H), 3.98 (s, 3H), 3.85 (d, J=6.8 Hz, 1H), 3.28-3.21 (m, 1H), 2.96-1.89 (m, 2H), 1.69-1.59 (m, 4H), 1.41-1.23 (m, 12H), 0.93 (d, J=6.8 MHz, 6H), m/z 507 (M+H)$^+$ Effects of the compounds synthesized as described above on SNAIL-p53 binding inhibition were confirmed in the following experiments.

Experimental Example 1

Confirmation of p53 Activity Recovery and Target Gene Induction

To confirm whether the compounds prepared according to Examples 1 to 5 are effective for inhibiting SNAIL-p53 binding at cell level, the compound was treated into K-Ras mutant cancer cell lines HCT116 and results were analyzed by western blotting.

Oncogenic K-ras suppresses the p53 activity through SNAIL. In the cell line HCT116, SNAIL is always expressed by K-Ras mutation and bound to p53 to suppress normal activity of p53. If the K-Ras mutant cancer cell line HCT116 is treated with a compound for suppressing SNAIL-p53 binding, p53 is normally activated and more expressed, and target genes of p53 are induced.

First, western blotting was performed to detect expression of p53 and p21, which is a target gene of p53. All cell lines used in the present invention were obtained from ATCC, and maintained in 10% FBS-containing RPMI-1640 or DMEM. Protein was extracted with RIPA buffer solution and a membrane loaded with cell lysate through typical SDS-PAGE and gel transfer method was prepared. After blocking with 5% non-fat dry milk, the membrane was subjected into a typical western blot procedure with an antibody corresponding to each gene. Antibodies used herein were obtained from Cell signaling, SantaCruz. p53 activity was confirmed by expression of p21, which is a target gene of p53. FIG. 1 shows images and graphs showing western blot results of HCT116 cells, K-Ras mutant cancer cell lines, using some of the compounds of Examples 1 to 5, and numeral values of the results are shown in Table 3 below.

enhanced expression of p53 and p21 as a target gene of p53 by the compounds indicates that functions of SNAIL are suppressed by the compounds in K-Ras mutant HCT116 cell lines in which SNAIL is always activated and SNAIL-p53 binding inhibition is maintained.

Experimental Example 2

Confirmation of SNAIL-p53 Binding Inhibiting Effect

Subsequently, among compounds that induced p53 and p21 and showed strong expression, compounds 5o and 7a were selected to identify relationships among K-Ras, SNAIL, and p53. To prove the SNAIL-p53 binding inhibition, GST pull down assay was performed using compounds 5o and 7a.

GST pull down assay is a method for identifying a binding degree of two proteins. GST-fused SNAIL protein and p53 recombinant protein were prepared and treated with the compound 5o or 7a to identify a binding degree of GST-SNAIL protein and p53 protein. Nutlin-3 was used as a control for the compounds. Nutlin-3 is known as a protein that blocks binding between p53 and MDM2, which is used as a negative control factor of p53, and is over-expressed in various tumor cells. If MDM2 is over-expressed, proteolysis of p53 is induced to suppress apoptosis occurring through target genes of p53, and an anti-proliferation effect of cells is induced. Although MDM2 is a representative control factor of p53, MDM2 is not applied to K-Ras mutant disease or mutant p53 containing disease.

To perform GST pull down assay, three human SNAIL fragments (residues 1-90, 91-112, and 113-264) and p53 fragments (1-93 and 93-292) were expressed in *E. coli* as GST-fusion protein. Each of the fragments was loaded on to GSH-agarose, washed, and then eluted using a buffer containing 20 mM reduced glutathione. The eluted fractions were purified using an anionexchange chromatography (HitrapQ). The recombinant human p53 protein (residues 94-292) was expressed in *E. coli* using the vector pET28A which contains a hexa-histidine tag at the C terminus. The p53 protein including the hexa-histidine tag was purified using Ni-NTA affinity and a size exclusion chromatography (Superdex 200). To confirm the direct binding between p53 and SNAIL, agarose-bead conjugated GST or GST-SNAIL was incubated with His-p539 (histidine-p53) in PBS for 45 minutes at 4° C.. After washing with PBS, the precipitated protein was subjected into SDS-PAGE and western blotting.

TABLE 3

| Gene | Control DMSO control | Protein expression ratio of compound to control | | | | | | | | | | | |
|------|---------|-----|-----|-----|-----|-----|-----|-----|-----|-----|-----|-----|-----|
|      |         | 5i  | 5j  | 5k  | 5l  | 5n  | 5m  | 5o  | 5p  | 8   | 7b  | 7a  | 6a  | 6b  |
| p53  | 1.0     | 1.6 | 1.3 | 0.3 | 0.6 | 1.1 | 0.8 | 2.6 | 1.6 | 2.3 | 4.6 | 4.2 | 1.9 | 4.0 |
| p21  | 1.0     | 4.6 | 5.0 | 0.2 | 0.1 | 0.2 | 0.1 | 2.5 | 0.3 | 1.7 | 7.0 | 7.2 | 2.8 | 8.7 |

Figure 20:
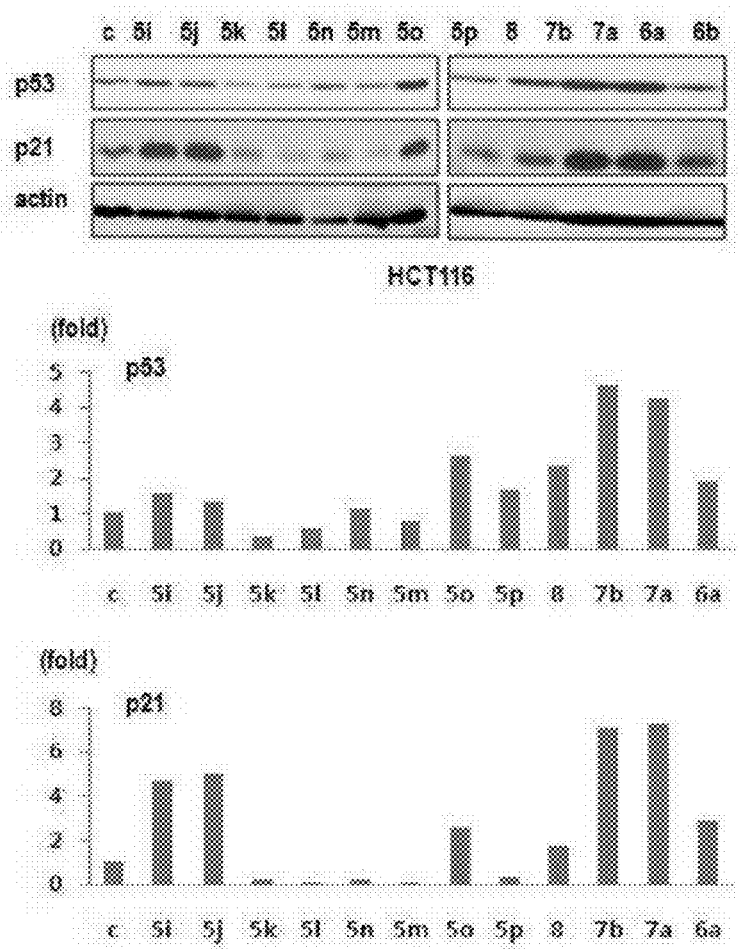
FIG. 20 shows western blot assay results for identifying an induction capability of compounds synthesized according to Examples 1 to 5.
Figure 21:
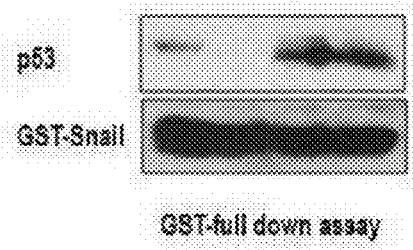

Referring the treatment results of the compounds at a concentration of 10 μM into K-Ras mutant HCT116 cancer cell lines, one of the compounds showed p53 expression 2 to 5 times stronger than that of a DMSO control and another compound showed p21 expression 2 to 8 times stronger than that of the DMSO control (see FIG. 20 and Table 3). The As shown in FIG. 21, GST pull down assay results show that in the case of control (c), the binding between GST-SNAIL and p53 was strong. Since Nutlin-3 also controls MDM2 and induces p53 activity, it did not inhibit SNAIL-p53 binding and showed the similar binding degree to that of the control. In contrast, in fractions using the compounds 5o and 7a, the binding between GST-SNAIL protein and p53 was substantially weak. This result shows that the compounds inhibited SNAIL-p53 binding.

Experimental Example 3

Confirmation of K-Ras Dependent p53 Induction Capability

To confirm that the compounds did not affect normal cells, and selectively affected only K-Ras mutant cancer cells to induce apoptosis, cytotoxicity and apoptosis effects of the compounds 5o and 7a were confirmed through cell vitality, by counting the number of cells using a tryphan blue solution. To confirm that the p53 induction of the compounds is related to K-Ras, A549 and HCT116, which are K-Ras mutant cancer cell lines, and MKN45, which is K-Ras wild type cancer cell line, were used.

Figure 22:
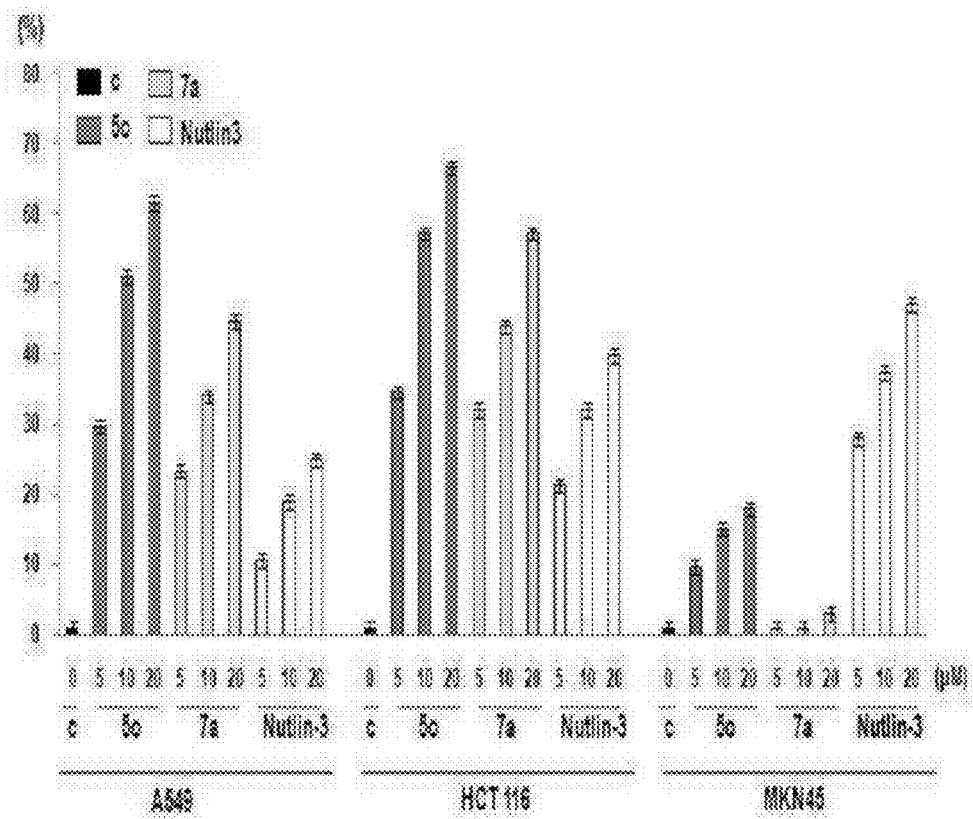
FIG. 22 shows apoptosis rates when K-Ras mutant cancer cell lines and K-Ras wild type cancer cell lines are treated with compounds 5o and 7a and Nutlin-3.

Table 4 shows numeral values of death rates of the respective cell lines, and FIG. 22 is a graph showing the numeral values of death rates.

implies that the compounds selectively affect only K-Ras damaged cancer cells and are thus useful for patients who develop cancer by K-Ras damage. On the other hand, results of Nutlin-3 did not have consistency. That is, Nutlin-3 showed death rates of 19% and 32% respectively in A549 and HCT116, which are K-Ras mutant cancer cell lines, at the same concentration of 10 µM, and showed a cell death rate of 38% in MKN45, which is K-Ras wild type cancer cell line, at the same concentration of 10 µM. As described above, it was confirmed that Nutlin-3 did not show a significant reactivity regardless of normal state or mutant state of K-Ras and did not show a selective reactivity to K-Ras. Thus, it was confirmed that differentially from Nutlin-3, the compounds 5o and 7a selectively affect K-Ras.

Experimental Example 4

Induction of Target Genes of p53 Activity

Then, the effect of compound 5o on mutant p53 was checked.

TABLE 4

| Type of cancer cell | Control (%) Control (DMSO) | Cancer cell death rate of compounds with respect to control (%) | | | | | | | | |
|---|---|---|---|---|---|---|---|---|---|---|
| | | 5o | | | 7a | | | Nutlin-3 | | |
| | 0 µM | 5 µM | 10 µM | 20 µM | 5 µM | 10 µM | 20 µM | 5 µM | 10 µM | 20 µM |
| A546 (k-Ras mutant) | 1 ± 1.3 | 30 ± 4.5 | 51 ± 1.1 | 62 ± 1.7 | 23 ± 3.4 | 34 ± 2.3 | 45 ± 2.3 | 11 ± 4.0 | 19 ± 4.5 | 25 ± 4.7 |
| HCT116 (k-Ras mutant) | 1 ± 1.2 | 35 ± 3.2 | 57 ± 1.6 | 67 ± 2.5 | 32 ± 2.1 | 44 ± 2.5 | 57 ± 2.8 | 21 ± 2.4 | 32 ± 2.9 | 40 ± 3.1 |
| MKN45 (k-Ras wild type) | 1 ± 1.1 | 10 ± 2.9 | 15 ± 2.4 | 18 ± 1.9 | 1 ± 1.0 | 1 ± 1.0 | 3 ± 2.4 | 28 ± 2.2 | 38 ± 2.9 | 47 ± 2.2 |

Figure 23:
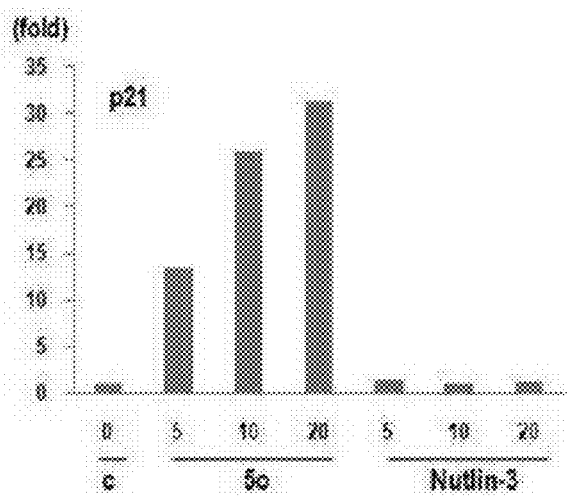
FIG. 23 is a graph of western blot assay results that p21 activity is induced by treating compound 5o and Nutlin-3 into p53 mutant cell lines.

Referring to the results obtained through cell death rates, in A549 and HCT116, which are K-Ras mutant cancer cell lines, the compound 5o showed, at the same concentration of about 10 µM, death rates of about 51% and about 57%, respectively, and the compound 7a showed, at the same concentration of about 10 µM, death rates of about 34% and about 44%, respectively (see Table 4 and FIG. 22). In contrast, differentially from in the K-Ras mutant cancer cell lines, in MKN45, which is K-Ras wild type cancer cell line, at the same concentration of about 10 µM, the compound 5o showed a death rate of about 15%, and the compound 7a showed a death rate of about 1%. These results show that the compounds selectively affect only cancer cell lines in which K-Ras is not normally activated and show high death rates. This result The compound 5o was treated into mutant p53-type MT/WT-p53 gene-containing MDA-MB 468, a human breast cancer cell line, and western blotting was performed. FIG. 23 shows a graph showing western blot results when the compound 5o was treated into MDA-MB, and Table 5 shows numeral values of the graph.

TABLE 5

| Gene | Control (DMSO control) | Expression ratio of gene to control with respect to compound 5o | | | Control (DMSO control) | Expression ratio of gene to control with respect to Nutlin-3 | | |
|---|---|---|---|---|---|---|---|---|
| | 0 µM | 5 µM | 10 µM | 20 µM | 0 µM | 5 µM | 10 µM | 20 µM |
| p21 | 1.0 | 13.5 | 25.9 | 31.3 | 1.0 | 1.4 | 0.9 | 1.2 |

When the compound 5o and Nutlin-3 were treated into p53 mutant-type cancer cell lines MDA-MB 468, expression of p21 was strong only when treated with the compound 5o (see FIG. 23 and Table 5). The result shows that Nutlin-3 did not affect p21 as a target gene in the presence of mutant p53, and differentially from the Nutlin-3, the compound 5o induced activity of p21.

Experimental Example 5

Xenograft In Vivo

1. Experimental Method

Athymic mouse was obtained from Daehan Biolink Co. Ltd, and raised under temperature and light conditions (20-23° C., cycle of 12 hours light/12 hours darkness) and fed with sterile diet and water freely. After 2 weeks, 1×10$^7$ A549 cells were inoculated into the athymic mouse (n=21) by intraperitoneal injection. After 2 weeks, each group was divided into three subgroups and PBS, and 10 mg/kg or 20 mg/kg of the compound 5o were intraperitoneally injected once per week for 10 weeks, and vitality thereof was measured. This animal test was approved by the Animal Protection Committee of Pusan National University, and performed according to a guideline presented by the same.

2. Experimental Results

Figure 24:
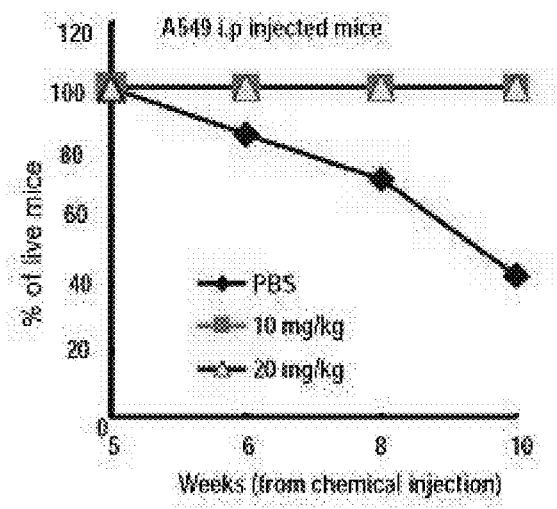
FIG. 24 shows a survival rate of a mouse treated with compound 5o after A549 cells were injected into athymic mouse through intraperitoneal injection.
Figure 25:
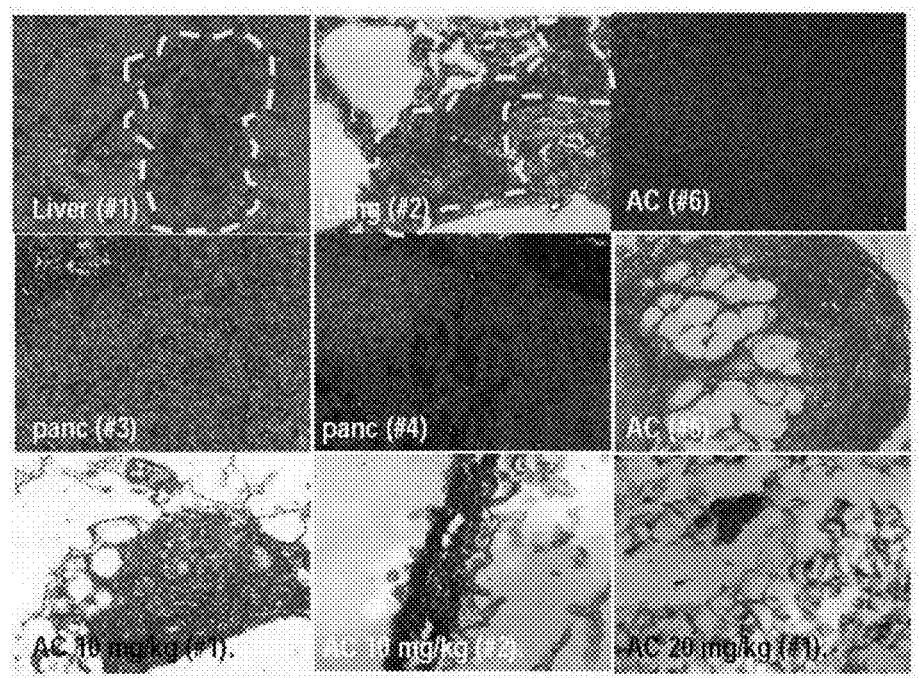
FIG. 25 shows a tissue image of a tumor generated through intraperitoneal injection.
Figure 26:
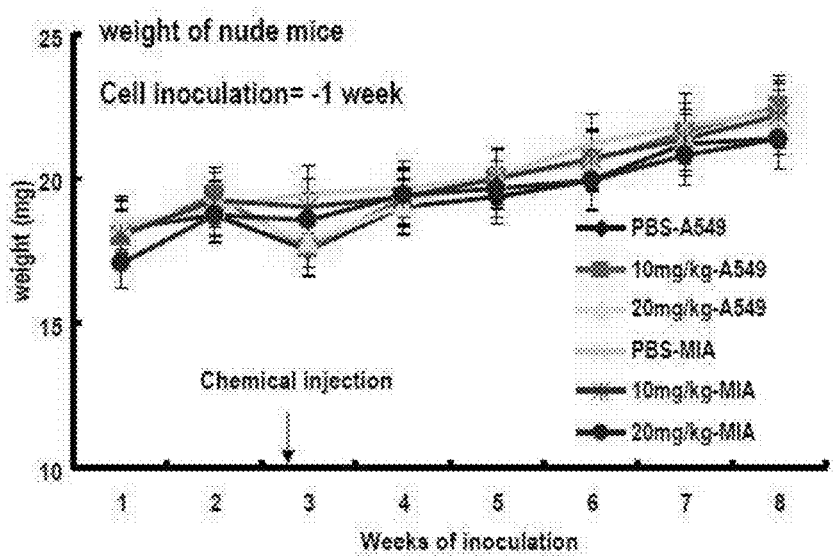
FIG. 26 shows an overall anatomical abnormal finding according to treatment with compound 5o in A549 cells.
Figure 26:
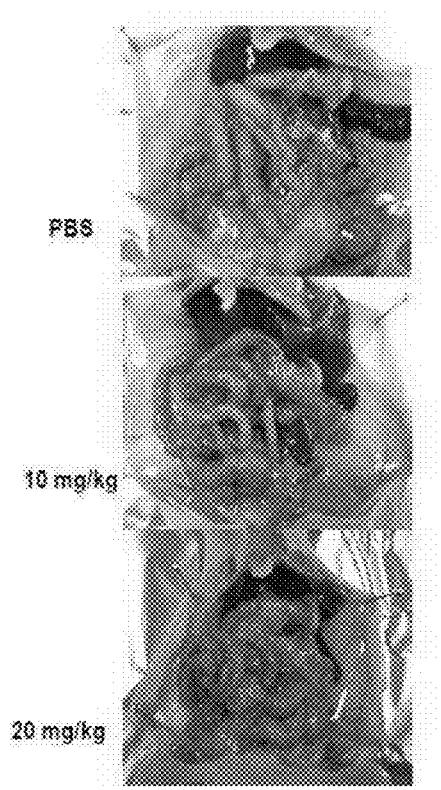

As shown in FIG. 24, when 10 mg/kg and 20 mg/kg of the compound 5o was treated, tumor-caused death was prevented. On the other hand, vitality of the PBS treatment group after 10 weeks was equal to or lower than 50%, and as shown in FIG. 25, the group treated with the compound 5o showed almost no tumor. In addition, as shown in FIG. 26, an overall anatomical abnormal finding according to weight loss or injection of the compound was not observed. Table 6 shows tumor development sites and morphological characteristic thereof.

TABLE 6

| Tumor site | Control | 10 mg/kg | 20 mg/kg |
|---|---|---|---|
| Liver | 1 (death) | 0 | 0 |
| Lung | 1 (death) | 0 | 0 |
| Pancreas | 2 (1/2 death) | 0 | 0 |
| A.C | 2 | 3 (regression) | 2 (regression) |

[Sequence List Pre Text]

SEQ ID NO: 1 shows an amino acid sequence of human p53 cellular tumor antibody.

What is claimed is:

1. A method of screening a therapeutic agent for K-Ras mutant cancer, comprising:
   immobilizing the DNA binding fragment of human p53 on an ELISA plate;
   adding the human SNAIL middle region protein fragment having amino acids 91-112 to the plate comprising the immobilized DNA binding fragment of human p53 fragment; and
   detection the extent of binding of the human SNAIL middle region fragment to the immobilized DNA binding fragment of the human p53 fragment in the presence, as well as the absence of a candidate drug,
   wherein if the binding in the presence of the drug is determined to be lower, the drug is considered a candidate for the therapeutic agent for treatment of K-Ras mutant driven cancer.

2. A method of screening a candidate compound for inhibiting SNAIL-p53 binding, comprising:
   immobilizing the DNA binding fragment of human p53 on an ELISA plate;
   adding the human SNAIL middle region protein fragment having amino acids 91-112 to the plate comprising the immobilized DNA binding fragment of human p53 fragment; and
   detecting the extent of binding of the human SNAIL middle region fragment to the immobilized DNA binding fragment of the human p53 fragment in the presence, as well as the absence of the candidate compound,
   wherein if the binding in the presence of the compound is determined to be lower, the compound is considered a candidate for inhibiting the SNAIL-p53 binding.

* * * * *

```
SEQUENCE LISTING

<160> NUMBER OF SEQ ID NOS: 1

<210> SEQ ID NO 1
<211> LENGTH: 393
<212> TYPE: PRT
<213> ORGANISM: Homo sapiens

<400> SEQUENCE: 1

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
            85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
```

```
                        225                     230                     235                     240
Ser Cys Met Gly Gly Met Asn Arg Arg Pro Ile Leu Thr Ile Ile Thr
                245                     250                     255

Leu Glu Asp Ser Ser Gly Asn Leu Leu Gly Arg Asn Ser Phe Glu Val
                260                     265                     270

Arg Val Cys Ala Cys Pro Gly Arg Asp Arg Arg Thr Glu Glu Glu Asn
                275                     280                     285

Leu Arg Lys Lys Gly Glu Pro His His Glu Leu Pro Pro Gly Ser Thr
        290                     295                     300

Lys Arg Ala Leu Pro Asn Asn Thr Ser Ser Ser Pro Gln Pro Lys Lys
305                     310                     315                     320

Lys Pro Leu Asp Gly Glu Tyr Phe Thr Leu Gln Ile Arg Gly Arg Glu
                        325                     330                     335

Arg Phe Glu Met Phe Arg Glu Leu Asn Glu Ala Leu Glu Leu Lys Asp
                340                     345                     350

Ala Gln Ala Gly Lys Glu Pro Gly Gly Ser Arg Ala His Ser Ser His
                355                     360                     365

Leu Lys Ser Lys Lys Gly Gln Ser Thr Ser Arg His Lys Lys Leu Met
        370                     375                     380

Phe Lys Thr Glu Gly Pro Asp Ser Asp
385                     390
```